(12) United States Patent
Mizuguchi

(10) Patent No.: US 8,679,994 B2
(45) Date of Patent: Mar. 25, 2014

(54) METHOD OF INSPECTING SYNTHETIC SILICIA GLASS MOLDED BODY

(71) Applicant: Nikon Corporation, Tokyo (JP)

(72) Inventor: Masafumi Mizuguchi, Yokohama (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 13/961,499

(22) Filed: Aug. 7, 2013

(65) Prior Publication Data

US 2013/0320219 A1 Dec. 5, 2013

Related U.S. Application Data

(62) Division of application No. 13/567,837, filed on Aug. 6, 2012, now Pat. No. 8,539,793, which is a division of application No. 11/885,510, filed as application No. PCT/JP2006/302172 on Feb. 8, 2006, now abandoned.

(30) Foreign Application Priority Data

Mar. 1, 2005 (JP) .................................. 2005-056108

(51) Int. Cl.
 *C03C 3/06* (2006.01)
 *G01N 23/00* (2006.01)
(52) U.S. Cl.
 USPC ............................................... 501/54; 65/378
(58) Field of Classification Search
 USPC ............................ 501/54; 65/377, 378, 29.12
 See application file for complete search history.

(56) References Cited

U.S. PATENT DOCUMENTS

| | | | |
|---|---|---|---|
| 4,358,306 A | 11/1982 | Okamoto et al. | |
| 5,086,352 A * | 2/1992 | Yamagata et al. | 359/350 |
| 5,229,336 A | 7/1993 | Akiyama et al. | 501/56 |
| 5,325,230 A * | 6/1994 | Yamagata et al. | 359/350 |
| 5,970,746 A | 10/1999 | Fujinoki et al. | 65/102 |
| 6,209,354 B1 | 4/2001 | Fujinoki et al. | 65/102 |
| 6,557,378 B2 | 5/2003 | Takagi et al. | 65/26 |
| 7,063,826 B2 | 6/2006 | Katsuro et al. | 423/335 |
| 7,312,170 B2 | 12/2007 | Nishimura et al. | 501/54 |
| 7,827,824 B2 | 11/2010 | Otsuka et al. | 65/104 |

(Continued)

FOREIGN PATENT DOCUMENTS

| | | |
|---|---|---|
| EP | 0 673 888 A1 | 9/1995 |
| EP | 1 340 722 A1 | 9/2003 |

(Continued)

OTHER PUBLICATIONS

European Search Report dated Jun. 24, 2010 in corresponding European Patent Application 06713315.7.

(Continued)

*Primary Examiner* — Noah Wiese

(57) ABSTRACT

A method of inspecting a synthetic silica glass molded body includes: irradiating the synthetic silica glass molded body with a spectrum line of an Hg lamp having a wavelength of 248 nm; measuring light emitted by the synthetic silica glass molded body; and a procedure which may include screening a portion which satisfies a condition that a ratio of the bright line intensity and the fluorescent light intensity is of a certain value or less, or which may include determining whether a condition that a ratio of a minimum value and a maximum value of a measured fluorescent light intensity is in a certain range is satisfied or not.

4 Claims, 5 Drawing Sheets

(56) References Cited

U.S. PATENT DOCUMENTS

| | | | |
|---|---|---|---|
| 2002/0050152 A1 | 5/2002 | Fujiwara et al. | |
| 2003/0051507 A1* | 3/2003 | Ikuta et al. | 65/30.1 |
| 2003/0129494 A1 | 7/2003 | Kaneda et al. | 429/231.1 |
| 2003/0171203 A1 | 9/2003 | Komine et al. | 501/54 |
| 2003/0190276 A1 | 10/2003 | Unehara et al. | 423/335 |
| 2005/0103053 A1 | 5/2005 | Segill et al. | 65/60.3 |
| 2007/0004579 A1* | 1/2007 | Bookbinder et al. | 501/54 |

FOREIGN PATENT DOCUMENTS

| | | |
|---|---|---|
| JP | 60-39535 | 3/1985 |
| JP | 9-235134 | 9/1997 |
| JP | 2001-72428 | 3/2001 |
| JP | 2001-97734 | 4/2001 |
| JP | 2001-114530 | 4/2001 |
| JP | 2001-180963 | 7/2001 |
| JP | 2003-81654 | 3/2003 |
| JP | 2004-307266 | 11/2004 |

OTHER PUBLICATIONS

M. Shimbo et al., "380 nm Photoluminescence Caused by Trace Na Impurity in High-Purity Synthetic Silica Glass", Japanese Journal of Applied Physics, 1993, vol. 32, pp. 671-673.

R. Debnath et al., "Dual Luminescence of $Cu^+$ in Glass", Journal of Non-Crystalline Solids, 1990, vol. 123, pp. 271-274.

International Preliminary Report on Patentability issued in corresponding International Patent Application No. PCT/JP2006/302172, mailed on Sep. 20, 2007.

International Search Report issued in corresponding International Patent Application No. PCT/JP2006/302172, mailed on May 23, 2006.

Restriction Requirement mailed from the Unites States Patent and Trademark Office on Jul. 5, 2011 in the related U.S. Appl. No. 11/885,510.

Office Action mailed from the Unites States Patent and Trademark Office on Sep. 27, 2011 in the related U.S. Appl. No. 11/885,510.

Office Action mailed from the Unites States Patent and Trademark Office on May 4, 2012 in the related U.S. Appl. No. 11/885,510.

Office Action mailed from the Unites States Patent and Trademark Office on Nov. 21, 2012 in the related U.S. Appl. No. 13/567,637.

Notice of Allowance mailed from the Unites States Patent and Trademark Office on Apr. 2, 2013 in the related U.S. Appl. No. 13/567,637.

U.S. Appl. No. 13/567,837, filed Aug. 6, 2013, Masafumi Mizuguchi et al., Nikon Corporation.

U.S. Appl. No. 11/885,510, filed May 2, 2008 Masafumi Mizuguchi et al., Nikon Corporation.

* cited by examiner

US 8,679,994 B2

METHOD OF INSPECTING SYNTHETIC SILICIA GLASS MOLDED BODY

CROSS-REFERENCE TO RELATED APPLICATIONS

This application is a divisional application filed under 37 C.F.R. §1.53(b) claiming priority benefit of U.S. application Ser. No. 13/567,837, filed on Aug. 6, 2012, issued, which claims priority benefit of U.S. application Ser. No. 11/885,510, filed on May 2, 2008, abandoned. This application also claims the priority benefit under 35 U.S.C. §371, of PCT International Application Number PCT/JP2006/302172, filed Feb. 8, 2006, which claimed foreign priority benefit to Japanese Application No. 2005-056108 filed Mar. 1, 2005 in Japan, the contents of all of which are incorporated herein by reference.

BACKGROUND

1. Field

The present invention relates to a synthetic silica glass molded body, a method of molding a synthetic silica glass molded body, and a method of inspecting a synthetic silica glass molded body, and, in more details, relates to a synthetic silica glass molded body which is used as a material for producing, for example, a photomask and an optical parts including a lens, a prism, a window, and the like which are used in an exposure apparatus using a light source such as an ultraviolet laser such as an excimer laser, an Hg lamp, and the like, and relates to a method of molding and a method of inspecting a synthetic silica molded body.

2. Description of the Related Art

In order to transfer an integrated circuit pattern such as an IC and an LSI, a downsized projection exposure apparatus (or photolithography apparatus) is mainly used. A wide exposure area and a higher resolution entirely covering such an exposure area are required for the projection optical system used in such a downsized projection exposure apparatus with an increase in the integration degree of the integrated circuit. Then, the countermeasures including the reduction in an exposure wavelength or the increase in the number of numerical aperture (NA) of the projection optical system are taken to improve the resolution of the projection optical system.

As an exposure light source, the i-line (365 nm) of an Hg lamp, as well as the KrF (248 nm) excimer laser and the ArF (193 nm) excimer laser which is a deep ultraviolet light source are mainly used at present in a liquid crystal display exposure apparatus and in a semiconductor exposure apparatus, respectively.

An optical member which can be used in such an exposure light source having a short wavelength and high irradiance is limited. In some parts of the liquid crystal display exposure apparatus provided with the above described exposure light source, a synthetic silica glass member is used as an optical member. In the semiconductor exposure apparatus provided with the above described exposure light source, a synthetic silica glass member is mainly used as an optical member. Such a synthetic silica glass member is an essential material in imaging optics of the downsized projection exposure apparatus because the synthetic silica glass member has high transmittance in an ultraviolet wavelength region and high resistance to long time exposure to the ultraviolet light.

Moreover, another important factor required to print a circuit on a wafer using a downsized projection exposure apparatus includes a reticle (photomask). In the photomask, the thermal expansion of a substrate due to the increase in the temperature is a major problem in addition to the ultraviolet transmittance and resistance, so a material having a small thermal expansion coefficient is required. For this reason, in the photomask, the synthetic silica glass member is used as the most important material.

For example, the direct method which is one of chemical vapor deposition (CVD) methods is used as a production method of such a synthetic silica glass. Here, the direct method refers to a method in which the silica glass is obtained as follows. A combustion-supporting gas (oxygen-containing gas, for example oxygen gas) and a combustible gas (hydrogen-containing gas, for example, hydrogen gas or natural gas) are mixed and burned with a burner made of silica glass. On the other hand, a high purity silicon compound (for example, silicon tetrachloride gas) as a raw gas is diluted by a carrier gas (usually oxygen gas), and the raw gas thus obtained is jetted from the center of the burner. Then, the raw gas is reacted (hydrolyzed) by the burning the oxygen gas and the hydrogen gas therearound to form fine particles of silica glass. The fine particles of silica glass are deposited on a target comprised of an opaque silica glass plate which is located beneath the burner to be turned, swung, and pulled down. At the same time, the particles of silica glass are melted and vitrified by the combustion heat of the oxygen gas and hydrogen gas. In the production method of the silica glass using the direct method as described-above, the solid is directly synthesized from a gaseous raw material. Accordingly, very high purity synthetic silica glass can be obtained. That is, the silica glass block synthesized by the CVD method has extremely high purity, high transmittance, and high resistance to ultraviolet irradiation. However, it has been relatively difficult to produce the synthetic silica glass having a desired form, especially having a large diameter, by the synthetic silica glass production method using the direct method.

On the other hand, in recent years, a synthetic silica glass member having a large surface area in a large sized lens, a photomask, a large-size flat panel display device, and the like has been necessitated. Then, in order to produce the synthetic silica glass member having a large surface area, the synthetic silica glass block obtained by the above described production method is molded by pressing it while heating. In the synthetic silica glass production method by molding and pressing the synthetic silica glass while heating, the synthetic silica glass molded body is molded as follows. The synthetic silica glass block is molded while accommodated in a mold and pressed with a pressing plate while being heated therein. Then, it is gradually cooled in the mold, and further annealed to mold a synthetic silica glass molded body having an enlarged opposed area and a predetermined form. However, in such a heating and pressing molding method, impurity contamination occurs in the synthetic silica glass due to the contact between the synthetic silica glass block and the mold which takes place in a heating and pressing molding process. As a result, there is a problem that the transmittance and irradiation resistance of the obtained synthetic silica glass molded body is reduced. Thus, it is not desirable to use the synthetic silica glass molded body in which impurity contamination has occurred as a material of an optical member for an exposure apparatus. Moreover, there is another problem that the impurity contamination is spread in a very wide region in the synthetic silica glass molded body because the impurity contamination occurs when the synthetic silica glass block is heated to a high temperature and when the temperature is maintained for a long period of time. For this reason, such an impurity contamination has been a serious problem, which causes the notable reduction in the yield of an optical member produced using the synthetic silica glass molded body as the material.

Japanese Unexamined Patent Application Publication No. 2003-81654, discloses a method of producing a synthetic silica glass which is characterized in which, in the step of heating a preform or molded body of the synthetic silica glass produced by the direct method or soot method, the heat treatment is performed while the preform or molded body of the synthetic silica glass is accommodated and heated in a container which is made of a carbon material containing Cu in a concentration of 0.1 ppm or less, and which is previously heat-treated at 1200° C. or more under a reduced pressure or an inert gas atmosphere. However, such a method of producing a synthetic silica glass is not sufficient to prevent the above described impurity contamination.

On the other hand, in some cases, the impurity contamination causes additive fluorescent light to be observed in a synthetic silica glass member at the time of exposure, as well as it causes deterioration in a quality such as transmittance and irradiation resistance. Such an observed additive fluorescent light may not necessarily be inhibited strictly as the variation in transmittance and laser damage because it does not cause the irradiance of exposure light to directly be varied unlike the variation in transmittance and laser damage. In actual, when the KrF excimer laser light and the ArF excimer laser light which have a high energy density of about 50 $mJ/(cm^2 \cdot pulse)$ or more are irradiated to the synthetic silica glass member, it actually does not happen that fluorescent light is not observed at all. This is because the sensitivity of fluorescent light is drastically high as compared to other physical properties (for example, transmittance), as well as because the structural defect such as non-bridging oxygen contained in the glass causes the fluorescent light. However, fluorescent light possibly causes flare which reduces the sharpness of a line pattern. Accordingly, it is preferable that the intensity of fluorescent light be as low as possible in practical use.

Japanese Unexamined Patent Application Publication No. 2001-114530 describes that impurities and the like which reduce the transmittance and irradiation resistance of the synthetic silica glass member in an ultraviolet wavelength area are typified by the transition metal elements including Fe, Ni, Cr, Mn, and the like, as well as, in a deep ultraviolet wavelength area such as the ArF excimer laser, alkaline metal elements such as Na and halogens such as CI also have an influence on the transmittance of the synthetic silica glass member in an ultraviolet wavelength area. As fluorescent light generated due to the impurity contamination, a fluorescent light band having a center wavelength of 380 nm generated by Na and a green color fluorescent light band having a center wavelength of 500 nm generated by Cu are typically known (See M. Shimbo et. al., Japanese Journal of Applied Physics, 1993, vol. 32, p. L671-L673 and R. Debnath and S. Kumar, J. Non-Crystal. Sol., 1990, vol. 123, p. 271-p. 274).

Japanese Unexamined Patent Application Publication No. 2001-72428 discloses a synthetic silica glass having 0.01 or less of a ratio of fluorescent light emission intensity relative to the intensity of a scattering light generated from a synthetic silica glass, the ratio being determined by irradiating the synthetic silica glass with an ultraviolet light having a wavelength ranging from 150 nm to 400 nm. Moreover, Japanese Unexamined Patent Application Publication No. Sho 60-39535 describes a silica glass screening method which is characterized in that the existence of copper in a silica glass is detected by means of fluorescent light.

Furthermore, as the fluorescent light which is emitted by a synthetic silica glass molded body, yellow (yellowish green) fluorescent light with a wide band having a center wavelength of 550 nm is observed some time after the KrF excimer laser is irradiated. However, the cause of the emission of yellow (yellowish green) fluorescent light has not been cleared as far as the present inventor investigated.

SUMMARY

The present invention has been made in consideration of the problems in prior art as described above. It is an object of the present invention to provide: a method of molding a synthetic silica glass molded body which makes it possible to obtain, surely and with high efficiency, a synthetic silica glass molded body in which a defective portion due to impurity contamination is fully prevented from occurring irrespective of the fact that the method is a method of molding a synthetic silica glass molded body by heating and pressing molding method; a synthetic silica glass molded body which makes it possible to improve a yield of a high quality synthetic silica glass member used in an exposure apparatus in which the light having a short wavelength of 400 nm or less is used as an exposure light; and a method of inspecting a synthetic silica glass member which makes it possible to screen a defective portion due to impurity contamination which is present in the synthetic silica glass molded body.

The present inventor has devoted to repeat studies so as to achieve the above object. As a result, it has been discovered that, in a method of molding the synthetic silica glass molded body by accommodating a synthetic silica glass block in a mold provided with a pressing portion, and by pressing the block while heating, it becomes possible to obtain, surely and with high efficiency, a synthetic silica glass molded body in which a defective portion due to impurity contamination is fully prevented from occurring, by previously washing the synthetic silica glass block so that concentrations of copper and aluminium which are present on the surface of the synthetic silica glass block is at a predetermined value or less, by previously supplying high purity carbon powders in the mold and heating the mold, and by molding the synthetic silica glass block by pressing the block while heating under a predetermined temperature condition, thus resulting in the completion of the present invention.

In order to seek the cause of a yellow fluorescent light which the synthetic silica glass molded body emits when the synthetic silica glass molded body is irradiated with a ultraviolet light, the present inventor investigated in detail the correlation between the amount of the impurities in a synthetic silica glass molded body and the intensity of the fluorescent light emitted from the synthetic silica glass member at the time of irradiating the ultraviolet light with respect to each element.

In such an investigation, firstly, a synthetic silica glass molded body which was produced by the conventional heating and pressing molding method was irradiated with a 254 nm spectrum line of an Hg lamp at an irradiance of 10 $mW/cm^2$. Thereafter, the fluorescent light which was emitted from the synthetic silica glass molded body was measured. As a result of such a measurement, a green fluorescent light having a center wavelength of 500 nm was observed from the surface of the synthetic silica glass molded body to a depth of about 20 mm to 30 mm. An region in which such a green fluorescent light is observed is supposedly called a contaminated region. Then, the KrF excimer laser light having a wavelength of 248 nm was irradiated to the contaminated region at a repetition frequency of 100 Hz and in an energy density of 100 mJ/(cm²·pulse). Thereafter, the fluorescent light emitted from the synthetic silica glass molded body was measured. The measurement of such a fluorescent light was made by means of a commercially available optical fiber type of a fluorescence spectrophotometer in combination with visual observation, and the luminescence of fluorescent light was recorded as a spectrum. In such measurement, immediately after the irradiation with the KrF excimer laser light was started, intense green fluorescent light having a center wavelength of 500 nm was observed as in the case where the 254 nm spectrum line of the Hg lamp was irradiated. When the KrF excimer laser light was continuously irradiated in about $3 \times 10^4$ pulses or more, the color of the fluorescent light was varied from green to yellow (yellowish green). Such a change in the color of fluorescent light occurred because the intense green fluorescent light having a center wavelength of 500 nm was reduced, while the intensity of yellow fluorescent light having a broad wavelength having a center of 550 nm was increased. FIG. 1 shows a graph showing the relationship between the fluorescent light intensity of such a fluorescent light spectrum and a wavelength. The green fluorescent light observed in the above manner is reduced by half immediately after the KrF excimer laser light is irradiated. Thus, a fluorescent light to which attention should be paid in practical use is rather such a yellow fluorescent light. When the excitation spectrum of the yellow fluorescent light was measured by means of a fluorescence spectrophotometer, an excitation band having a center wavelength of 270 nm and having a tail spreading to about 320 nm was obtained. This excitation band approximately coincided with the excitation band of the green fluorescent light.

The relationship between the intensity of the above yellow fluorescent light and the concentration of the impurities contained in the synthetic silica glass molded body was investigated. The result of such an investigation was summarized in a graph showing the relationship between the intensity of yellow fluorescent light and the impurity concentration. The graph in FIG. 2 shows the relationship between the intensity of yellow fluorescent light and the concentration of copper (Cu). The graph in FIG. 3 shows the relationship between the intensity of yellow fluorescent light and the concentration of sodium (Na). The graph in FIG. 4 shows the relationship between the intensity of yellow fluorescent light and the concentration of iron (Fe). Note that, each concentration of the above impurities (Cu, Na, Fe) was analyzed by ICP-MS. As apparent from the graph shown in FIG. 4, the correlation between the concentration of iron which is a typical transition metal element and the intensity of yellow fluorescent light was not established at all. As apparent from the graph shown in FIG. 3 also, the correlation between sodium, one of impurities which is the most easily mixed in the synthetic silica glass molded body and the intensity of yellow fluorescent light was not recognized. On the other hand, as apparent from the graph shown in FIG. 2, the correlation between the concentration of copper and yellow fluorescent light was recognized. However, small fluctuation was seen in the correlation. As a result, it was estimated that only copper did not cause fluorescent light.

Consequently, further discussion was made about the correlation between the yellow fluorescent light and the impurity concentration. According to the aforementioned literature (R. Debnath and S. Kumar, J. Non-Crystal, Sol., 1990. vol. 123, p. 271-p. 274), from the fact that green fluorescent light is emitted from the above contaminated region immediately after the irradiation of the laser light, it is estimated that Cu in the state of monovalence is mixed in at an early stage. It is well known that a monovalent ion, for example, a sodium ion ($Na^+$), tends to be mixed in, together with an aluminium ion ($Al^{+3}$), quartz other than silica glass. This is caused by the fact that $Al^{+3}$ can be considered to lack one positive electric charge as compared to $Si^{4+}$ which is a member ion of $SiO_2$, and accordingly $Al^{+3}$ has a high affinity with a monovalent cation to compensate the lacked positive electric charge. When, base on the above theory, the correlation between the relationship between the concentrations of copper ([Cu]) and aluminium ([Al]) as well as the intensity of yellow fluorescent light was determined, it was found that a very definite correlation is established between a value calculated by using an equation of $[Cu]+0.03\times[Al]$ and the intensity of yellow fluorescent light. FIG. 5 shows a graph showing the relationship between the value calculated by using such an equation of $[Cu]+0.03\times[Al]$ and the intensity of yellow fluorescent light. However, in silica glass in which aluminium is not substantially detected, but in which 0.2 wt.ppb or more of copper is detected, green fluorescent light emitted from silica glass is observed by irradiating an Hg lamp light. Thus, it is estimated that Al itself does not emit fluorescent light, but Al only plays a roll of an increaser of fluorescent light (an increaser which increases quantum efficiency of emitting a light) or a stabilizer (a stabilizer which chemically stabilizes an emission center). It is estimated that, for example, when Cu is contained alone in a silica glass, Cu which serves as an emission center tends to be changed in a state where Cu no longer serves as the emission center due to the effect of room temperature, exposure to sun light, or the like. In contrast, when Al is contained together with Cu, Al plays a roll of the stabilizer of fluorescent light, and thereby enables Cu to stably be present and to still serve as an emission center.

Subsequently, the relationship between a green fluorescent light and a yellow fluorescent light was investigated. It was described above that the intensity of yellow fluorescent light is increased as the intensity of green fluorescent light is reduced. Here, the measured reduction ($\Delta Ig$) in the amount of green fluorescent light intensity is defined by the following equation (2):

$$\Delta Ig = Ig_0 - Ig_i \qquad (2)$$

where $Ig_0$ is the intensity of green fluorescent light immediately after the start of irradiation, and $Ig_i$ is the intensity of green fluorescent light after the irradiation of a predetermined number of pulses. On the other hand, the measured increase ($\Delta Iy$) in the amount of yellow fluorescent light intensity is defined by the following equation (3):

$$\Delta Iy = Iy_i - Iy_0 \qquad (3)$$

where $Iy_0$ is the intensity of yellow fluorescent light immediately after the start of irradiation, and $Iy_i$ is the intensity of yellow fluorescent light after the irradiation of a predetermined number of pulses. Then, $\Delta Iy$ was plotted as the function of $\Delta Ig$ calculated as shown above. FIG. 6 shows a graph showing the relationship between $\Delta Ig$ and $\Delta Iy$. As apparent from the graph shown in FIG. 6, a very definite correlation is recognized between $\Delta Ig$ and $\Delta Iy$. It is estimated from the correlation between $\Delta Ig$ and $\Delta Iy$ that a photochemical reaction occurs due to the irradiation of KrF excimer laser light, thus resulting in the change from the origin of green fluorescent light to the origin of yellow fluorescent light. The present inventor has also found that the intensity of yellow fluorescent light is increased relative to the green fluorescent light when the synthetic silica glass molded body is molded somewhat in an oxidizing atmosphere (at reduced pressure, nitrogen and oxygen flow) from a reducing atmosphere (at reduced pressure, nitrogen flow). Therefore, it is concluded that the origin of yellow fluorescent light is a divalent Cu. Specifically, the present inventor concluded that the cause of green fluorescent light is a monovalent copper ion ($Cu^+$) stabilized by an aluminium ion ($Al^{3+}$), and that the cause of yellow fluorescent light is a divalent copper ion ($Cu^{2+}$) formed by oxidation of a monovalent copper ion ($Cu^+$).

Furthermore, the present inventor investigated the contaminated region in more detail. Specifically, the distribution of the impurities in the contaminated region was precisely measured in association with a depth in the synthetic silica glass molded body. Note that, the term depth here refers to a length in a direction perpendicular to a surface of the synthetic glass molded body which has come into contact with the mold used in molding the synthetic silica glass molded body, in a case where the surface is defined as a depth position of 0. In such measurement, different samples were obtained at depth intervals of 3 mm in the synthetic silica glass molded body by cutting out cylinders having a diameter of 30 mm from the intended surface of the molded synthetic silica glass molded body, and by slicing the cylinders 3 mm in a thickness. Then, the distribution of the impurity concentration was measured by chemically analyzing each sample by means of ICP-MS (detection lower limit: 0.1 wt.ppb). FIG. 7 shows a graph showing the relationship between the impurity concentration obtained in the measurement and the depth in the synthetic silica glass molded body. It was found from the distribution of each impurity shown in FIG. 7 that Cu which was the origin of yellow fluorescent light was diffused in almost the same depth as Na which was one of elements the most easily diffused in the synthetic silica glass molded body. Moreover, to a depth of about 18 mm of the samples, in which about 0.2 wt.ppb of Cu was detected, green fluorescence was clearly observed when the light of an Hg lamp was illuminated. On the other hand, in the region of the samples at a depth of around 20 mm where the green fluorescent light was observed very slightly, the concentration of Cu was lower than the sensitivity limit of the ICP, and thus Cu was not able to be detected. The above result showed that a detection method of the impurities in the synthetic silica glass by observing fluorescent light has higher detection sensitivity than the ICP-MS. In addition, due to the very large diffusion coefficient of Cu and to ultra-high sensitivity fluorescent light observation, a region in the synthetic silica glass molded body where a fluorescent light was observed was expanded to a large extent. This resulted in a large reduction in the yield of a synthetic silica glass member (for example, photomask and the like) which was obtained from the synthetic silica glass molded body as a material.

Studies were devotedly repeated to positively utilize these facts. As a result, it was discovered that it became possible to screen highly homogeneous synthetic silica glass members by observing a fluorescent light to inspect contaminated regions by impurities. That is, the purity of the member was guaranteed to a certain extent by screening, as a good quality article, regions which was so deep that Cu did not invade, i.e. regions in which green (yellow) fluorescent light was not observed, based on the fact that impurity cations which can invade deeply in the synthetic silica glass molded body like Cu include at most only Na and Li, and in addition that the observation of fluorescent light in the synthetic silica glass molded body allows the detection of the contaminated regions due to impurities with a drastically higher sensitivity than those of transmittance measurement and laser resistance measurement. As a result, the present invention has been completed.

Specifically, a method of molding a synthetic silica glass molded body of the present invention is a method of molding a synthetic silica glass molded body by accommodating a synthetic silica glass block in a mold provided with a pressing portion, and by pressing the block while heating, the method comprising:

a step of washing the synthetic silica glass block so that a concentration of copper which is present on the surface of the synthetic silica glass block is 2 ng/cm² or less, and so that a concentration of aluminium thereon is 10 ng/cm² or less, before accommodating the synthetic silica glass block in the mold;

a step of heating high purity carbon powders in which a content of copper is 40 wt.ppb or less and a content of aluminium is 100 wt.ppb or less at a temperature condition of 1200° C. to 1900° C.;

a step of heating the mold at a temperature condition of 1700° C. to 1900° C.;

a step of applying the high purity carbon powders after the heating step on the inner surface of the mold after the heating step, before accommodating the synthetic silica glass block in the mold; and a step of molding the synthetic silica glass block in a predetermined form by pressing the block by means of the pressing portion while heating so as to the temperature of the block can be within a hold temperature range of 1500° C. to 1700° C., after accommodating the washed synthetic silica glass block in the mold.

In the method of molding a synthetic silica glass molded body of the present invention, the heating temperature in the step of heating the high purity carbon powders is preferably in a condition of 1200° C. to 1600° C.

Moreover, in the method of molding a synthetic silica glass molded body of the present invention, the step of heating the high purity carbon powders and the step of heating the mold may simultaneously be performed.

Furthermore, in the method of molding a synthetic silica glass molded body of the present invention, a content of copper in the mold after the heating step is preferably 80 wt.ppb or less.

Moreover, in the method of molding a synthetic silica glass molded body of the present invention, the applied amount of the high purity carbon powders in the step of applying the high purity carbon powders is preferably 7 mg/cm² to 200 mg/cm².

Moreover, in the method of molding a synthetic silica glass molded body of the present invention, a concentration of OH group in the synthetic silica glass block is preferably 900 ppm to 1300 ppm by mass.

Furthermore, in the method of molding a synthetic silica glass molded body of the present invention, in the step of molding the synthetic silica glass block, the silica glass block is preferably pressed in the predetermined form by means of the pressing portion so that a maximum pressure can be 0.2 Kg/cm² to 1.0 Kg/cm².

A synthetic silica glass molded body of the present invention is a synthetic silica glass molded body molded by accommodating a synthetic silica glass block in a mold provided with a pressing portion, and by pressing the block while heating, wherein, in at least 60% by volume or more of a region of the synthetic silica glass molded body, conditions that:

a concentration of copper is 0.2 wt.ppb or less and a concentration of aluminium is 10 wt.ppb or less; and the concentrations of copper and aluminium are represented by the following equation $$[Cu]+0.03\times[Al]<0.4 \text{ wt.ppb} \quad (1)$$

(where [Cu] shows the concentration (wt. ppb) of copper, and [Al] shows the concentration (wt. ppb) of aluminium.) are satisfied.

Moreover, the region preferably satisfies a condition that a ratio of a bright line intensity of a spectrum line having a wavelength of 254 nm and a fluorescent light intensity from a green to a yellow fluorescent light having a center wavelength of 500 nm to 600 nm (fluorescent light intensity/bright line intensity) is 0.005 or less in visible-ultraviolet spectra which are obtained by measuring in a direction perpendicular to an irradiation direction of a spectrum line, when the region is irradiated with the spectrum line of an Hg lamp having a wavelength of 254 nm, at an irradiance condition of 10 mW/cm$^2$ or more, which has been transmitted through a filter for blocking the visible light or reducing an intensity thereof.

Furthermore, the region preferably satisfies a condition that a ratio of a minimum value and a maximum value of a fluorescent light intensity (minimum/maximum) is 0.2 to 1.0 when measuring the fluorescent light intensity of yellowish green fluorescent light having a center wavelength of 550 nm which is generated by irradiating a KrF excimer laser light over the entire surface area of the region perpendicular to an irradiation direction of the KrF excimer laser light after the region is irradiated with $3\times10^4$ pulses of the KrF excimer laser light having a wavelength of 248 nm at a repetition frequency of 100 Hz and in an energy density of 100 mJ/(cm$^2$·pulse).

An inspection method of a synthetic silica glass molded body of the present invention comprises:

a step of irradiating the synthetic silica glass molded body with a spectrum line of an Hg lamp having a wavelength of 254 nm, at an irradiance condition of 10 mW/cm$^2$ or more, which has been transmitted through a filter for blocking a visible light or reducing an intensity thereof;

a step of measuring, in a direction perpendicular to the irradiation direction of the spectrum line, an intensity of a bright line having a wavelength of 254 nm emitted by the synthetic silica glass molded body, and a fluorescent light intensity from a green to a yellow fluorescent light having a center wavelength of 500 nm to 600 nm emitted by the synthetic silica glass molded body; and a step of screening a portion which satisfies a condition that a ratio of the bright line intensity and the fluorescent light intensity (fluorescent light intensity/bright line intensity) is 0.005 or less.

Moreover, in the method of inspecting a synthetic silica glass molded body of the present invention, a measurement surface of the synthetic silica glass molded body is preferably previously polished.

A method of inspecting a synthetic silica glass member of the present invention comprises:

a step of irradiating a synthetic silica glass member with $3\times10^4$ pulses of a KrF excimer laser light having a wavelength of 248 nm at a repetition frequency of 100 Hz and in an energy density of 100 mJ/(cm$^2$·pulse);

a step of measuring a fluorescent light intensity of yellowish green fluorescent light having a center wavelength of 550 nm emitted by the synthetic silica glass member over the entire surface area of the synthetic silica glass member perpendicular to the irradiation direction of the KrF excimer laser light; and a step of determining whether a condition that a ratio of a minimum value and a maximum value of the fluorescent light intensity of the yellowish green fluorescent light (minimum/maximum) is 0.2 to 1.0 is satisfied or not.

Moreover, in the method of inspecting a synthetic silica glass member of the present invention, the step of irradiating the KrF excimer laser light is preferably performed in an aluminium-made chamber purged with a nitrogen gas.

According to the present invention, it becomes possible to provide: a method of molding a synthetic silica glass molded body which makes it possible to obtain, surely and with high efficiency, a synthetic silica glass molded body in which a defective portion due to impurity contamination is fully prevented from occurring irrespective of the fact that the method is a method of molding a synthetic silica glass molded body by heating and pressing molding method; a synthetic silica glass molded body which makes it possible to improve a yield of a high quality synthetic silica glass member used in an exposure apparatus in which the light having a short wavelength of 400 nm or less is used as an exposure light; and a method of inspecting a synthetic silica glass member which makes it possible to screen a defective portion due to impurity contamination which is present in the synthetic silica glass molded body.

BRIEF DESCRIPTION OF THE DRAWINGS

The above objects and features of the present invention will be more apparent from the following description of some preferred embodiments with reference to the accompanying drawings, wherein.

DESCRIPTION OF EMBODIMENTS

Figure 1:
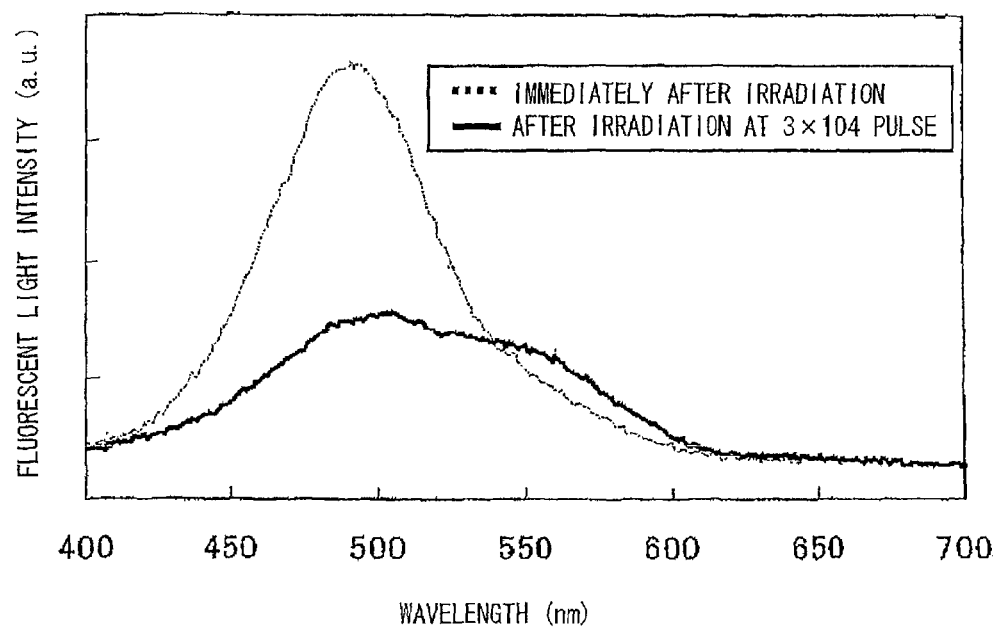
FIG. 1 is a graph showing the relationship between an intensity of a broad yellow fluorescent light spectrum having a center wavelength of 550 nm and a wavelength.
Figure 2:
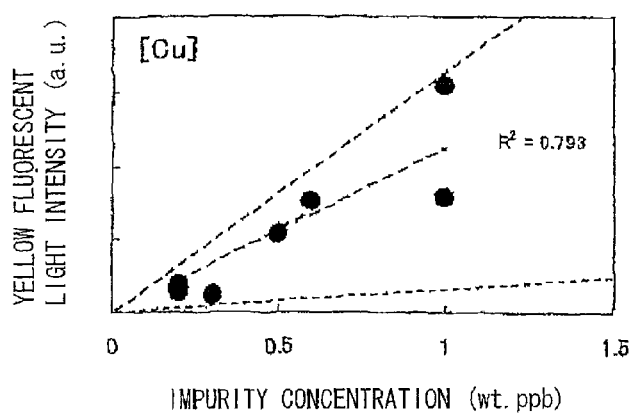
FIG. 2 is a graph showing the relationship between the intensity of yellow fluorescent light and a concentration of copper (Cu).
Figure 3:
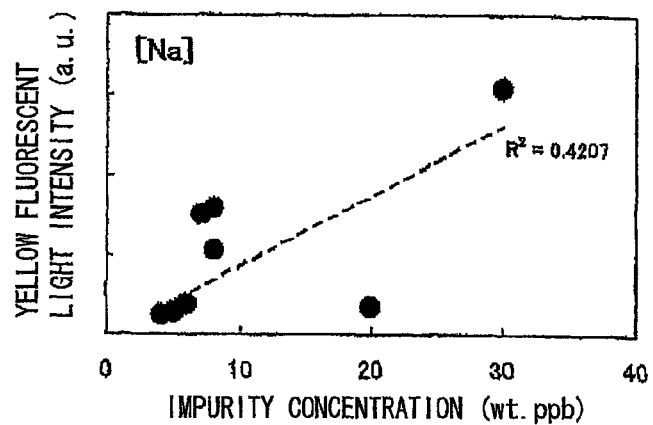
FIG. 3 is a graph showing the relationship between the intensity of yellow fluorescent light and a concentration of sodium (Na).
Figure 4:
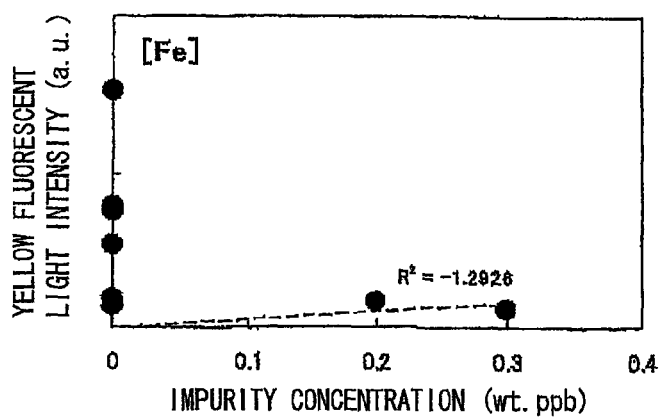
FIG. 4 is a graph showing the relationship between the intensity of yellow fluorescent light and a concentration of iron (Fe).
Figure 5:
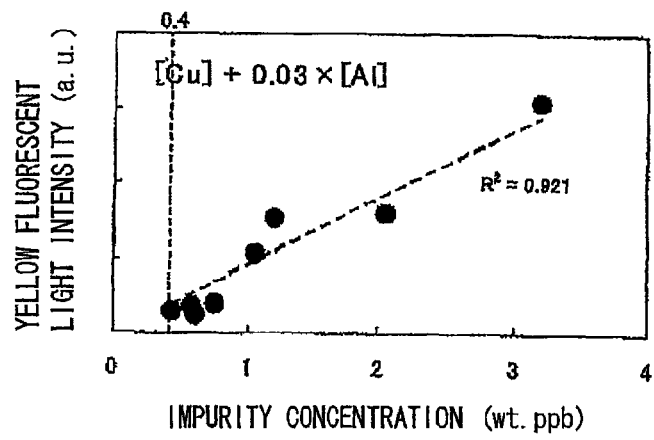
FIG. 5 is a graph showing the relationship between the value calculated based on an equation of $[Cu]+0.03\times[Al]$ and the intensity of yellow fluorescent light.
Figure 6:
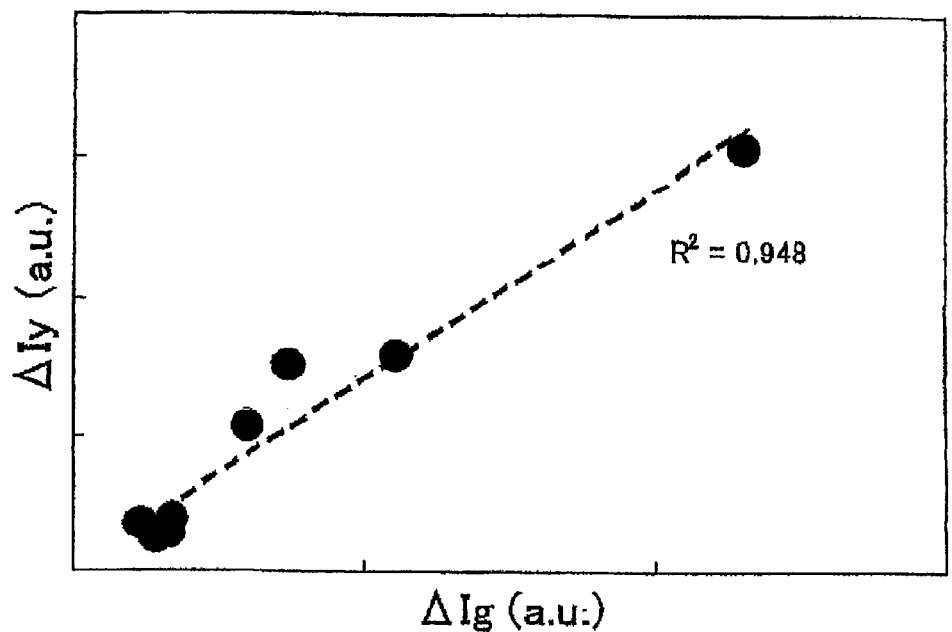
FIG. 6 is a graph showing the relationship between ΔIg and ΔIy.
Figure 7:
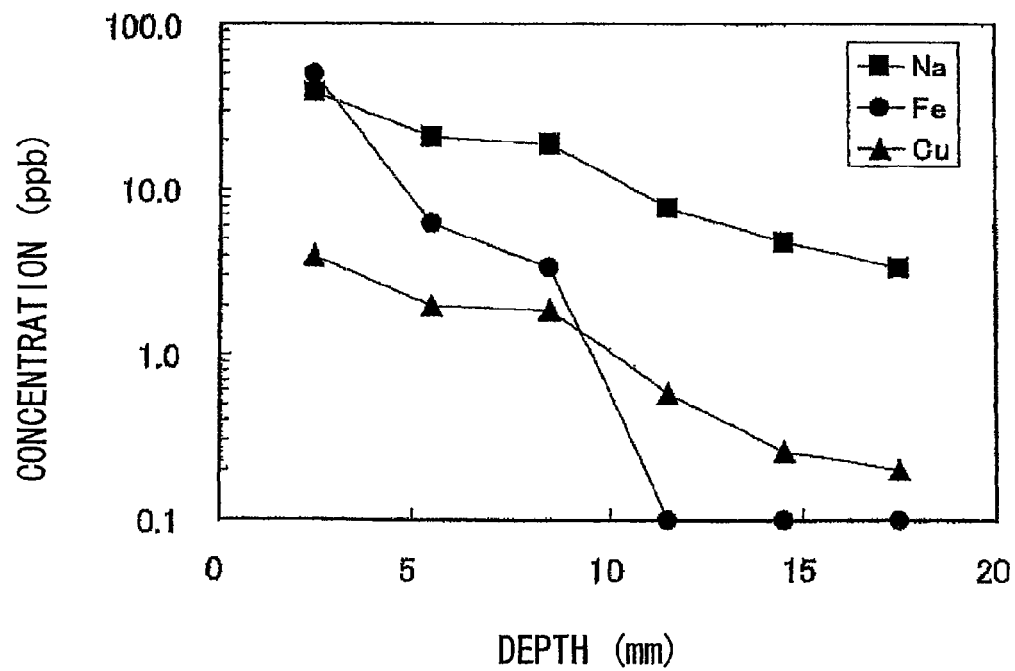
FIG. 7 is a graph showing the relationship between the impurity concentration and a depth in the synthetic silica glass molded body.

The suitable embodiments of the present invention will hereinafter be described in detail.

Firstly, a method of molding a synthetic silica glass molded body of the present invention will be described. That is, a method of molding a synthetic silica glass molded body of the present invention is a method of molding a synthetic silica glass molded body by accommodating a synthetic silica glass block in a mold provided with a pressing portion, and by pressing the block while heating, the method comprising:

a step (i) of washing the synthetic silica glass block so that a concentration of copper which is present on the surface of the synthetic silica glass block is 2 $ng/cm^2$ or less, and so that a concentration of aluminium thereon is 10 $ng/cm^2$ or less, before accommodating the synthetic silica glass block in the mold;

a step (ii) of heating high purity carbon powders in which a content of copper is 40 wt.ppb or less and a content of aluminium is 100 wt.ppb or less at a temperature condition of 1200° C. to 1900° C.;

a step (iii) of heating the mold at a temperature condition of 1700° C. to 1900° C.;

a step (iv) of applying the high purity carbon powders after the heating step on the inner surface of the mold after the heating step, before accommodating the synthetic silica glass block in the mold; and a step (v) of molding the synthetic silica glass block in a predetermined form by pressing the block by means of the pressing portion while heating so as to the temperature of the block can be within a hold temperature range of 1500° C. to 1700° C., after accommodating the washed synthetic silica glass block in the mold.

Here, the synthetic silica glass block used in the present invention is first described. The synthetic silica glass block used in the present invention is preferably a high purity synthetic silica glass block produced by using a chemical vapor deposition (CVD) method and the like. Of such a synthetic silica glass block, a synthetic silica glass block in which the concentration of OH group is 900 ppm to 1300 ppm by mass is preferable. The synthetic silica glass block having less than the lower limit of the above concentration range of the OH groups has a high viscosity of the synthetic silica glass block when a temperature of the entire synthetic silica glass block is within a relatively high temperature range, and therefore tends to be difficult to be molded. On the other hand, when a concentration of the OH groups exceeds the upper limit, the viscosity of the synthetic silica glass block is low, and thereby the surface of the glass bends inside, and thereby is entangled. As a result, many inferior portions tend to be caused.

Next, the step (i) will be described. The step (i) according to the present invention is a step of washing the synthetic silica glass block so that a concentration of copper which is present on the surface of the synthetic silica glass block is 2 $ng/cm^2$ or less, and so that a concentration of aluminium thereon is 10 $ng/cm^2$ or less, before accommodating the synthetic silica glass block in the mold.

As compared to the case where a synthetic silica glass molded body is molded using a synthetic silica glass block whose surface has been washed in the above manner, when a synthetic silica glass molded body is molded using a synthetic silica glass block whose surface has not been washed in the above manner, a contaminated region in the obtained synthetic silica glass molded body is expanded about 4 to 5 times, resulting in the notable reduction in the yield of portions which are not contaminated. When the synthetic silica glass molded body is molded using the synthetic silica glass block whose surface has not been washed, the contaminated region in the obtained synthetic silica glass molded body is still expanded through two or three times of molding the synthetic silica glass molded body using the synthetic silica glass block whose surface has been washed thereafter. This is because the synthetic silica glass block, the surface of which has been contaminated, is accommodated in a furnace, and molded by heat, and thereby notably contaminates the interiors of the mold and the molding furnace.

Such a suitable method of cleaning includes a method in which the synthetic silica glass block is immersed in a 10%-by-weight aqueous solution of hydrofluoric acid for 24 hours or more, and then fully rinsed with pure water, and a method in which a commercially available bleach (for example, one containing about 4% of NaClO and about 1% of NaOH) is applied on the synthetic silica glass block, left to stand for 3 hours or more, and then fully rinsed with pure water. Such washing makes it possible to reduce impurity-contaminated region in the synthetic silica glass molded body in which a fluorescent light is clearly observed.

Using such hydrofluoric acid and the like as a detergent makes it possible to surely wash the synthetic silica glass block so that the concentrations of copper and aluminium which are present on the surface of the synthetic silica glass block are 2 $ng/cm^2$ or less and 10 $ng/cm^2$ or less, respectively. Note that sufficient effect is not obtained by using a commercially available detergent containing hydrochloric acid as a main component. The cause for this is that hydrochloric acid cannot fully remove the organic contamination on the surface of the block.

The concentrations of copper and aluminium present on the surface of the synthetic silica glass block after the washing is 2 $ng/cm^2$ or less and 10 $ng/cm^2$ or less, respectively. More than the upper limit of the concentrations of copper and aluminium causes the contaminated region in the obtained synthetic silica glass molded body to expand. Note that these concentrations can be determined by quantifying the concentration of each ion in a solution obtained by resolving a certain amount of area of a sample to a depth of about 1 μm using hydrofluoric acid by analyzing mean such as ICP and the like.

Subsequently, the step (ii) will be described. The step (ii) is the step of heating high purity carbon powders in which a content of copper is 40 wt.ppb or less and a content of aluminium is 100 wt.ppb or less at a temperature condition of 1200° C. to 1900° C.

In the high purity carbon powders used in the step (ii) according to the present invention, a content of copper is 40 wt.ppb or less and a content of aluminium is 100 wt.ppb or less. When the contents of copper and aluminium exceed the upper limit, the contaminated region due to impurities is widely expanded in the obtained synthetic silica glass molded body.

In the step (ii), the high purity carbon powders are heated (idle-heating) at a temperature condition of 1200° C. to 1900° C. The high purity carbon powders are further purified by such heating. Such high purity carbon powders have a far larger surface area per mass than that of the mold. Therefore, the effect achieved in the idle-heating is extremely large, thus being able to effectively inhibit contamination due to the copper in the obtained synthetic silica glass molded body.

Less than the lower limit of the above temperature condition in performing such heating does not allow the high purity carbon powders to sufficiently be purified. On the other hand, more than the upper limit causes the high purity carbon powders to be sintered with each other, resulting in the reduction in the performance as a dispersing agent. Note that, a period of time for which such heating is performed is preferably about 1 to 12 hours. A pressure applied during such heating is preferably about 10 Pa or less. Moreover, as described above, the high purity carbon powders have a far larger surface area per mass than that of the mold, and therefore can be purified by heating at a lower temperature condition than the heating temperature of the mold to be described below. Therefore, a temperature condition for such heating is preferably 1200° C. to 1600° C.

Then, the step (iii) will be described. The step (iii) is the step of heating the mold at a temperature condition of 1700° C. to 1900° C.

In the method of molding a synthetic silica glass molded body by heating and pressing molding method, impurities such as copper ooze from a mold made of carbon (graphite) also, which is used in molding, during heating at high temperatures. For this reason, in order to inhibit as strictly as possible the contamination due to the impurities such as copper which ooze from the mold, the mold is heated (so-called idle-heating) at a temperature condition of 1700° C. to 1900° C. The mold is purified by carrying out such heating.

Less than the lower limit of the temperature condition in carrying out such heating does not allow the mold to fully be purified. In contrast, more than the upper limit causes the mechanical strength of the mold to tend to be reduced. Note that a time period for which such heating is performed is preferably about 1 to 24 hours. A pressure applied during such heating is preferably about 10 Pa or less.

Incidentally, in the steps (ii) and (iii), the high purity carbon powders and the mold can be accommodated in the same furnace, and simultaneously heated.

Then, the step (iv) will be described. The step (iv) is the step of applying the high purity carbon powders after the heating step on the inner surface of the mold after the heating step, before accommodating the synthetic silica glass block in the mold.

As described above, in the method of molding a synthetic silica glass molded body by heating and pressing molding method, the impurities such as copper ooze from the mold also which is used in molding during heating at high temperatures. In order to inhibit as strictly as possible the contamination due to the impurities such as copper which ooze from the mold, it is easily considered to reduce the amount of the impurities such as copper and aluminium which are contained in the mold. However, it is difficult to obtain a ultra-high purity mold containing a small amount of impurities because a mold is generally made by baking and solidifying carbon powders, at a high temperature, which are connected to each other with a binder. On the other hand, carbon powders having much higher purity than that of the mold are commercially available. Therefore, in the present invention, the contamination due to impurities which ooze from the mold and the fusion by heating between the synthetic silica glass block and the mold are prevented from occurring by applying the high purity carbon powders after the heating step on the inner surface of the mold after the heating step.

A method of applying the high purity carbon powders after the heating step on the inner surface of the mold after the heating step is not particularly limited, and the example includes a method of applying the powders thinly and uniformly by means of a brush. In such a step, the amount of the high purity carbon powders which are applied on the inner surface of the mold is not particularly limited, but is preferably about 7 mg/cm$^2$ to 200 mg/cm$^2$.

The contamination due to the copper in the obtained synthetic silica glass molded body can notably be inhibited by the synthetic silica glass block whose surface has been washed as described in the step (i) and by heating (idle-heating) the mold and the high purity carbon powders, and by applying the high purity carbon powders after the heating step on the inner surface of the mold after the heating step as described in the steps (ii) to (iv), respectively. Note that, even when only a part of the surface washing step as described in the step (i), and the heating steps and the high-purity-carbon-powder applying step as described in the steps (ii) to (iv) is performed, a sufficient effect cannot be obtained. Therefore, it is important to perform all the steps (i) and (ii) to (iv) in molding the synthetic silica glass molded body by the heating and pressing molding method.

Then, the step (v) will be described. The step (v) is the step of molding the synthetic silica glass block in a predetermined form by pressing the block by means of the pressing portion while heating so as to the temperature of the block can be within a hold temperature range of 1500° C. to 1700° C., after accommodating the washed synthetic silica glass block in the mold.

Referring to drawings, a suitable embodiment for performing the step (v) will hereinafter be described in detail. Note that, in the following descriptions and drawings, the same reference numeral is given to the same or corresponding element. Overlapping descriptions are omitted.

Figure 8:
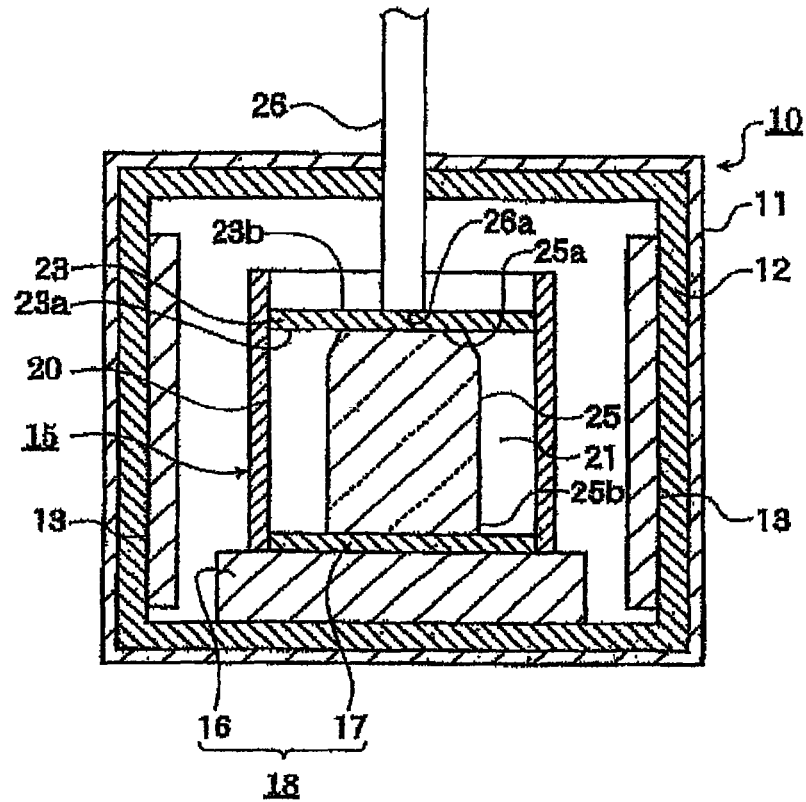
FIG. 8 is a schematic longitudinal sectional view showing an embodiment of a molding apparatus suitable for implementing a method of molding a synthetic silica glass molded body of the present invention.

FIG. 8 is a schematic longitudinal sectional view showing one embodiment of a suitable molding apparatus for performing the above steps.

In a molding apparatus 10 shown in FIG. 8, a thermal insulator 12 mounted on the entire inner wall of a metallic vacuum chamber 11, and a carbon heater 13 as heating means mounted on the longitudinal wall of the thermal insulator 12 are provided. Further a mold 15 is accommodated in the approximately central portion of the interior of the vacuum chamber 11.

The mold 15 is provided with a bottom section 18 provided with a bottom plate 16 and a receiving plate 17, and a side wall section 20 formed in a cylindrical form above the bottom section 18. A hollow portion 21 is defined by the cylindrical side wall section 20 and the bottom section 18.

A top plate 23 having the shape corresponding to that of the hollow portion 21 as a press portion is disposed in the hollow portion 21, and can be moved to the side of the bottom portion 18 of the mold 15 by pressing a press surface (top surface) 23b of the top plate 23 by means of a cylinder rod 26 of a hydraulic cylinder (not shown) mounted outside the vacuum chamber 11 as a press apparatus.

Note that, the hydraulic cylinder provided with the cylinder rod 26, which is constructed so as to be pressed to move by adjusting the oil pressure supplied from the outside, is omitted from the detailed drawing.

The mold 15 and top plate 23 have resistance to the heat and strength to the temperature and pressure during molding the synthetic silica glass block 25, and are formed of a material which is hard for impurities to getting mixed in with the synthetic silica glass block 25 even if contacting with the synthetic silica glass block 25 during molding. Graphite is preferably used as such a material. Moreover, the content of copper in the mold 15 is preferably 80 wt.ppb or less.

The aforementioned steps (ii) to (iv) have been performed on the interior of the mold 15. The high purity carbon powders after the heating are applied on the interior of the mold 15 which is heat as described above.

The synthetic silica glass block 25 accommodated in the hollow portion 21 of the mold is a synthetic silica glass in a block form which is previously synthesized by using a various types of production methods. The synthetic silica glass block which contains dissolved OH groups in a concentration of 900 ppm to 1300 ppm by mass as described above is preferably used. Note that, in the present embodiment, the synthetic silica glass block which has previously been washed in the aforementioned step (i) is used.

Description will be specifically made about a suitable method of molding a synthetic silica glass molded body using the molding apparatus 10.

First, the mold 15 is formed by combining the bottom plate 16, the receiving plate 17, and the side wall section 20 in the vacuum chamber 11. And, the synthetic silica glass block 25 is placed in the hollow portion 21 of the mold 15. The synthetic silica glass block 25 mentioned here is the one above described.

The synthetic silica glass block 25 accommodated in the mold 15 is preferably preheated so that the inside thereof is approximately uniformly heated in advance within a temperature range of 200° C. to 300° C. using unillustrated heating means. The preheating is performed at a temperature increasing rate of 10° C./min to 20° C./min, for example, when the synthetic silica glass block 25 weighs about 10 kg to 300 kg. This rate is maintained for a time period of, for example, for 10 to 20 minutes in which the synthetic silica glass block 25 is sufficiently heated to the inside thereof at a predetermined temperature within a temperature range of 200° C. to 300° C. Such heating means specifically includes an inert oven provided with a container, the interior of which can be made air-sealed, and replaced with an inert gas, as well as a heater equipped with a temperature adjuster. It is possible to reduce the heating time in the mold 15 by preheating the synthetic silica glass block 25 in the above manner. In particular, this is because if the preheating temperature is 200° C. to 300° C., an amount of hydrogen molecules in the synthetic silica glass block 25 tends to be hardly reduced during heating.

After the synthetic silica glass block 25 is accommodated in the hollow portion 21 of the mold, the top plate 23 is disposed above the synthetic silica glass block 25. Furthermore, a hydraulic cylinder is set such that a pressing portion 26a of the cylinder rod 26 abuts the pressing surface 23b of the top plate 23. Then, a pressure in the vacuum chamber 11 is reduced to 1 Pa to 10 Pa (preferably 1 Pa) using a vacuum pump to fill an inert gas (for example, pure nitrogen gas) in the vacuum chamber 11.

Next, the mold 15 and the synthetic silica glass block 25 accommodated in the hollow portion 21 are heated so that they are maintained within a temperature range of 1500° C. to 1700° C. by means of the carbon heater 13. The above maintaining temperature is preferably within a range of 1530° C. to 1630° C. When the maintaining temperature of the synthetic silica glass block is less than the above lower limit, the viscosity of the silica glass is high. As a result, it is difficult to mold the block. Therefore, it becomes difficult to obtain the synthetic silica glass molded body formed in the desired form. In contrast, when the maintaining temperature of the synthetic silica glass block is more than the above upper limit, a time period for which the synthetic silica glass block is exposed to high temperature is increased. As a result, the diffusion-by-heat of the impurities is increased, resulting in the wide diffusion of the impurities through the contact surface with the mold in the synthetic silica glass molded body.

Such a heating is performed as follows. That is, after the heating temperature is increased from the aforementioned preheating temperature to the predetermined temperature within the foregoing hold temperature range at a temperature increasing rate of 500° C./hr to 800° C./hr by causing the carbon heater 13 to generate heat, the predetermined temperature within the foregoing hold temperature range is maintained for a time period in which the block synthetic silica glass block 25 is sufficiently heated to the inside thereof so that the temperature of the block synthetic silica glass block 25 is approximately uniformly increased to the inside thereof at a hold temperature of 1500° C. to 1700° C. (preferably 1530° C. to 1630° C.).

Next, while the synthetic silica glass block 25 is maintained at the hold temperature after being heated, the cylinder rod 26 is moved downward by controlling the oil pressure applied to the hydraulic cylinder so that the press surface 23b of the top plate 23 is pressed by the press portion 26a of the cylinder rod 26. The top plate 23 is thereby moved in the press direction, that is, toward the bottom portion 18 of the mold 15 so that the block synthetic silica glass block 25 is press-molded between the press surface 23a of the top plate 23 and the bottom portion 18.

A maximum pressure for pressing the synthetic silica glass block 25 in this manner is preferably 0.2 kg/cm$^2$ to 1.0 kg/cm$^2$ and more preferably 0.2 kg/cm$^2$ to 0.8 kg/cm$^2$. Less than the lower limit of the maximum pressure is too low to deform the glass. It is therefore difficult to mold the synthetic silica glass molded body conforming to the form of the mold, particularly resulting in the tendency to increase a curvature radius at a corner. On the contrary, when the maximum pressure exceeds the upper limit, the thickness of an affected layer tends to be increased. Application of the maximum pressure allows the synthetic silica glass block 25 to be surely molded in the desired form, and the reduction in a time for molding the synthetic silica glass block 25 to be achieved.

In such a process of pressing, the pressure applied by the top plate 23 is small at an early stage of molding, and preferably then is increased so as to be largest at the final stage to perform pressing. For example, the pressure applied may gradually be increased as the top plate 23 is moved down. In addition, the small pressure at the early stage may be used to perform pressing until the molding is advanced to a predetermined degree, and then may be increased to a predetermined pressure. Furthermore, the stepwise increase in pressure may be selected. In this case, if the height direction position of a top 25a of the pre-mold synthetic silica glass block 25 (that is, the position in which the press surface 23a of the top plate 23 contacts the top 25a of the pre-mold synthetic silica glass block 25) is considered to be at 0% of displacement (deformation ratio), and if the height direction position of the top of the synthetic silica glass block 25 in a case where the synthetic silica glass block 25 has normally been molded without unmolded portion is considered to be at 100% of displacement (deformation ratio), a small pressure equivalent to the pressure at the early stage of molding can be used to perform pressing when the height displacement of the synthetic silica glass block 25 is within a range of, for example, 0% to 80%, preferably 0% to 50%. Such a stepwise increase in pressure for pressing the synthetic silica glass block 25 allows more uniform molding of the synthetic silica glass block.

At the early stage of molding, that is, at the stage at which the height displacement of the synthetic silica glass block 25 is within 0% to 50%, the area in which the synthetic silica glass block contacts the top plate 23 is small, and the volume which is deformed by pressing is also small. Therefore, a small pressure can be used to perform pressing. The preferable range of pressure for this pressing varies depending on the state of the synthetic silica glass block 25, and therefore it is preferable to suitably select the pressure at the time of molding. However, it is preferable to use 7% to 25% of the foregoing maximum pressure to perform pressing. For example, the pressure can be controlled so that a rate of the downward movement of the top plate 23 can be within a range of 0.1 mm/min to 8 mm/min to perform pressing.

The reason why small pressure is applied at the early stage of molding to perform pressing is that the application of large pressure forces the synthetic silica glass block 25 to be deformed, and resulting in tendency of the synthetic silica glass block 25 to be molded without uniformity, since the synthetic silica glass block 25 is easy to deform at the early stage of molding, and the displacement to the side of the top 25a of the synthetic silica glass block 25 therefore is large.

At the intermediate stage of molding, that is, at the stage at which the height displacement of the synthetic silica glass block 25 is within a range of 50% to 80%, the synthetic silica glass block 25 is so spread in the hollow portion 21 of the mold 15 that the synthetic silica glass block 25 is pressed by the large area of the press surface 23a of the top plate 23. At such an intermediate stage of molding, although the deformation of the synthetic silica glass block 25 is small, the silica glass contacts the press surface 23a in the large area thereof, resulting in the necessity of large force to deform the synthetic silica glass block 25. Therefore, at the intermediate stage of the molding, the pressure applied on the synthetic silica glass block 25 from the press surface 23a of the top plate 23 is preferably increased so as to be 25% to 60% of the maximum pressure described below to perform pressing. Application of such a pressure allows the synthetic silica glass block 25 to uniformly be molded, and, at the same time, to be deformed by the synthetic silica glass block 25 in a short time, resulting in the tendency to be achieve a reduced molding time.

At the final stage of molding, that is, at the stage at which the displacement of height direction position is within a range of 80% to 100%, the synthetic silica glass block 25 is spread in the approximately entire area in the cross-sectional direction of the hollow portion 21 of the mold 15, and therefore the pressing is performed using the approximately entire area of the press surface 23a of the top plate 23. At such a final stage of molding, the pressure applied from the press surface 23a of the top plate 23 is preferably controlled so as to be 60% to 100% of the foregoing maximum pressure to perform pressing from a point of view that pressure as high as possible is applied within a pressure range which can prevent the synthetic silica glass block 25 and the mold 15 from being damaged. From a point of view that the molding time is reduced further, the maximum pressure is more preferably controlled so as to be 0.3 Kg/cm$^2$ to 1.0 Kg/cm$^2$ to perform pressing, and particularly preferably 0.5 Kg/cm$^2$ to 1.0 Kg/cm$^2$.

Note that, in the obtained synthetic silica glass molded body, the depth in which the contaminated region due to impurities is diffused from the surface thereof is proportional to the diffusion time of the impurities (total time period of heating time in the above temperature increasing process, maintaining time elapsed at the hold temperature, and the molding time). Accordingly, the heating time in increasing the temperature is preferably 1 to 7 hours. The maintaining time elapsed at the hold temperature is preferably 0 to 2 hours. Furthermore, the molding time is preferably 0.5 to 3 hours. When such heating time, maintaining time, and molding time are respectively less than the lower limit, it tends to be difficult to fully perform molding. On the other hand, more than the upper limit tends to expand the thickness from the surface of contaminated region due to the impurities.

Then, the pressing by means of the top plate 23 is ended at the stage at which the synthetic silica glass block 25 is molded into the synthetic silica glass molded body of the predetermined form. Subsequently, while disposed in the hollow portion 21 of the mold 15, the molded synthetic silica glass molded body is cooled.

In a cooling process, cooling is preferably forced to be performed at a higher cooling rate than that at which standing to cool is performed after heating with the carbon heater 13 is stopped in the mold 15. As such a cooling method, a usual method can be used, but it is not particularly limited. For example, a method in which a pathway for a cooling medium to pass is mounted in the vacuum chamber 11 for the cooling medium can be included. Such a cooling allows reduction in the time for which the molded synthetic silica glass molded body is exposed to high temperatures.

In such a cooling process, while the temperature of the molded synthetic silica glass molded body is within a temperature range of the foregoing hold temperature to 1200° C., cooling is preferably performed at a cooling rate of 2° C./min to 3.5° C./min. Less than the lower limit of such a cooling rate causes the time for which the synthetic silica glass molded body is exposed to high temperatures to be so increased that the thickness of the affected layer tends to be increased. On the contrary, more than the upper limit causes the molded glass to tend to be broken with high possibility. Such a cooling allows the time for which the synthetic silica glass molded body is exposed to high temperatures to be reduced, and furthermore a leading time to be reduced.

In the cooling process, while the temperature of the molded synthetic silica glass molded body is within a temperature range of 1200° C. to 800° C., slow cooling is preferably gradually performed at a cooling rate of 1° C./min to 8° C./min until the temperature of the entire synthetic silica glass molded body is reduced to 800° C. from a point of view that the strain of the synthetic silica glass molded body should be reduced. Less than the lower limit of such a cooling rate allows the strain of the synthetic silica glass molded body to easily be reduced, but causes cooling time to be so increased that the time for which the synthetic silica glass molded body is exposed to high temperatures tends to be increased in excess. On the contrary, more than the upper limit causes the strain to be increased, and the possibility for the glass to be broken to tend to be increased. Note that, the cooling rate is preferably adjusted depending on various kinds of molding conditions in each of the temperature ranges.

In the cooling process, in the process in which cooling is continued until the temperature of the entire molded synthetic silica glass molded body is reduced to a temperature range of 800° C. to 100° C., cooling is preferably performed at a cooling rate of 4° C./min to 15° C./min. Less than the lower limit of such a cooling rate causes the time for which the synthetic silica glass molded body is exposed to high temperatures to be so increased that the thickness of the affected layer tends to be increased. On the contrary, more than the upper limit causes the molded glass to tend to be broken with high possibility. Such a cooling allows the time for which the silica glass is exposed to high temperatures to be reduced, and furthermore a leading time to be reduced. Note that, as a cooling method, the method same as that described above can be used.

At the stage at which the temperature of the synthetic silica glass molded body is sufficiently reduced by using such a cooling, the synthetic silica glass molded body is taken out of the vacuum chamber 11.

By using the above described molding method of a synthetic silica glass molded body of the present invention to mold the synthetic silica glass molded body, the synthetic silica glass molded body is molded within a relatively low temperature range of 1500° C. to 1700° C., and the time for raising and lowering temperature can be reduced. Thereby, it is possible to reduce the time for which the synthetic silica glass block 25 is exposed to higher temperatures. In addition, these make it possible to efficiently prevent the impurities from diffusing to the synthetic silica glass molded body, and also the amount of hydrogen molecules is prevented from being so reduced that the laser resistance thereof can be improved.

Such a possibility to reduce the time for which the synthetic silica glass block 25 is exposed to high temperatures can prevent the synthetic silica glass block 25 from reacting with the graphite of the mold 15. Furthermore, the difference in heat contraction occurred during cooling based on the difference in the coefficients of linear expansion between the synthetic silica glass block 25 and the mold 15 is reduced correspondingly to the reduction in the molding temperature, resulting in reduction in the stress which the mold 15 applies when compressing the synthetic silica glass block 25 during cooling. Therefore, the synthetic silica glass molded body which has a thin affected layer and a small birefringence can be obtained surely and with high efficiency.

Note that, the synthetic silica glass molded body molded by such a molding method is used as a material for various kinds of optical members, and preferably used as a material used to produce lenses, mirrors, a substrate for a reticle or the like on which a laser with a wavelength of 250 nm or less is irradiated. It is also particularly preferably used as a plate-like body having a large area used in a substrate for a reticle (photomask) such as a mask for a large-sized liquid crystal, a mask for a semiconductor and the like, and in the material of a large-sized lens of imaging optics, and as other large-sized glass block.

A suitable method of molding a synthetic silica glass molded body of the present invention has been described above. A synthetic silica glass molded body of the present invention will be described below.

A synthetic silica glass molded body of the present invention is a synthetic silica glass molded body molded by accommodating a synthetic silica glass block in a mold provided with a pressing portion, and by pressing the block while heating, wherein, in at least 60% by volume or more of a region of the synthetic silica glass molded body, conditions that:

a concentration of copper is 0.2 wt.ppb or less and a concentration of aluminium is 10 wt.ppb or less; and the concentrations of copper and aluminium are represented by the following equation (1):

$$[Cu]+0.03\times[Al]<0.4 \text{ wt.ppb} \tag{1}$$

(where [Cu] shows the concentration (wt. ppb) of copper, and [Al] shows the concentration (wt. ppb) of aluminium.) are satisfied.

The condition specified in the present invention that the condition that the concentration of copper is 0.2 wt.ppb or less and the concentration of aluminium is 10 wt.ppb or less is satisfied is obtained as a result of the discussion about the yellow fluorescent light observed when the ultraviolet light is irradiated on the synthetic silica glass molded body as described above and about the concentrations of copper and aluminium. When an optical member is produced using a portion containing more than 0.2 wt.ppb of copper concentration or more than 10 wt.ppb of aluminium concentration as materials, the produced optical member allows intense yellow fluorescent light to be observed when a KrF excimer laser light having a wavelength of 248 nm is irradiated thereon, and has a low transmittance and low laser-resistance. Note that, a method of measuring the concentrations of such copper and aluminium is not particularly limited, and includes, for example, an analysis method by ICP-MS.

The condition specified in the present invention that the condition that the concentrations of copper and aluminium are represented by the following equation (1):

$$[Cu]+0.03\times[Al]<0.4 \text{ wt.ppb} \tag{1}$$

(where [Cu] shows the concentration (wt. ppb) of copper, and [Al] shows the concentration (wt. ppb) of aluminium.) is satisfied is obtained as a result of the discussion about the correlation between yellow fluorescent light observed when the ultraviolet light is irradiated on the synthetic silica glass molded body as described above and the concentrations of copper and aluminium. When an optical member is produced using a portion, as a material, which satisfies the condition that the value of $[Cu]+0.03\times[Al]$ represented by the equation (1) is 0.4 wt.ppb or more, the produced optical member allows intense yellow fluorescent light to be observed when a KrF excimer laser light having a wavelength of 248 nm is irradiated thereon, and has a low transmittance and low laser-resistance. Accordingly, it is undesirable to use the portion which does not satisfy the condition represented by the equation (1) as the material for the production of a synthetic silica glass member used in an exposure apparatus using the light having a short wavelength of 400 nm or less as an exposure light.

The synthetic silica glass molded body of the present invention satisfies the above conditions in at least 60% by volume or more of the region of the synthetic silica glass molded body. The synthetic silica glass molded body of the present invention satisfies the above conditions in such a large region, and thereby allows the high yield production of a synthetic silica glass member (for example, photomask) used in an exposure apparatus using the light having a short wavelength of 400 nm or less as an exposure light.

The above region of the synthetic silica glass molded body according to the present invention preferably satisfies a condition that a ratio of a bright line intensity of a spectrum line having a wavelength of 254 nm and a fluorescent light intensity from a green to a yellow fluorescent light having a center wavelength of 500 nm to 600 nm (fluorescent light intensity/bright line intensity) is 0.005 or less in visible-ultraviolet spectra which are obtained by measuring in a direction perpendicular to an irradiation direction of a spectrum line, when the region is irradiated with the spectrum line of an Hg lamp having a wavelength of 254 nm, at an irradiance condition of 10 mW/cm² or more, which has been transmitted through a filter for blocking the visible light or reducing an intensity thereof.

The portion of the synthetic silica glass molded body in which the ratio of the bright line intensity of the spectrum line having a wavelength of 254 nm and the fluorescent light intensity of a green to a yellow fluorescent light having a center wavelength of 500 nm to 600 nm (fluorescent light intensity/bright line intensity) exceeds 0.005 allows intense yellow fluorescent light to be observed when the KrF excimer laser light having a wavelength of 248 nm is irradiated thereon, and therefore is not preferable as a material for the production of a synthetic silica glass member used in an exposure apparatus using the light having a short wavelength of 400 nm or less as an exposure light. If an optical member is produced using the portion, the produced optical member has a low transmittance and low laser-resistance. Note that, such a synthetic silica glass molded body of the present invention can be produced by using the above described method of molding a synthetic silica glass molded body of the present invention.

The above region of the synthetic silica glass molded body according to the present invention preferably satisfies a condition that a ratio of a minimum value and a maximum value of a fluorescent light intensity (minimum/maximum) is 0.2 to 1.0 when measuring the fluorescent light intensity of yellowish green fluorescent light having a center wavelength of 550 nm which is generated by irradiating a KrF excimer laser light over the entire surface area of the region perpendicular to an irradiation direction of the KrF excimer laser light after the region is irradiated with $3 \times 10^4$ pulses of the KrF excimer laser light having a wavelength of 248 nm at a repetition frequency of 100 Hz and in an energy density of 100 mJ/(cm²·pulse).

In a case where an optical member used in an exposure apparatus is produced using the portion of the synthetic silica glass molded body which does not satisfy the condition that the ratio of the minimum and maximum values (minimum/maximum) of the fluorescent light intensity of the yellowish green fluorescent light having a center wavelength of 550 nm is 0.2 to 1.0, the irradiance of the transmitted exposure light is made uneven when the exposure light is irradiated, and thereby the exposure performance is notably reduced. Thus, such a portion of the synthetic silica glass molded body is not preferable as a material used for the production of a synthetic silica glass member used in an exposure apparatus using the light having a short wavelength of 400 nm or less as an exposure light. Note that, such a synthetic silica glass molded body of the present invention can be produced by using the above described method of molding a synthetic silica glass molded body of the present invention.

A method of inspecting a synthetic silica glass molded body of the present invention will then be described. The method of inspecting a synthetic silica glass molded body comprises:

a step of irradiating the synthetic silica glass molded body with a spectrum line of an Hg lamp having a wavelength of 254 nm, at an irradiance condition of 10 mW/cm² or more, which has been transmitted through a filter for blocking a visible light or reducing an intensity thereof;

a step of measuring, in a direction perpendicular to the irradiation direction of the spectrum line, an intensity of a bright line having a wavelength of 254 nm emitted by the synthetic silica glass molded body, and a fluorescent light intensity from a green to a yellow fluorescent light having a center wavelength of 500 nm to 600 nm emitted by the synthetic silica glass molded body; and a step of screening a portion which satisfies a condition that a ratio of the bright line intensity and the fluorescent light intensity (fluorescent light intensity/bright line intensity) is 0.005 or less.

Based on the drawings, a suitable embodiment for performing each process of such an inspection method will be described below.

Figure 9:
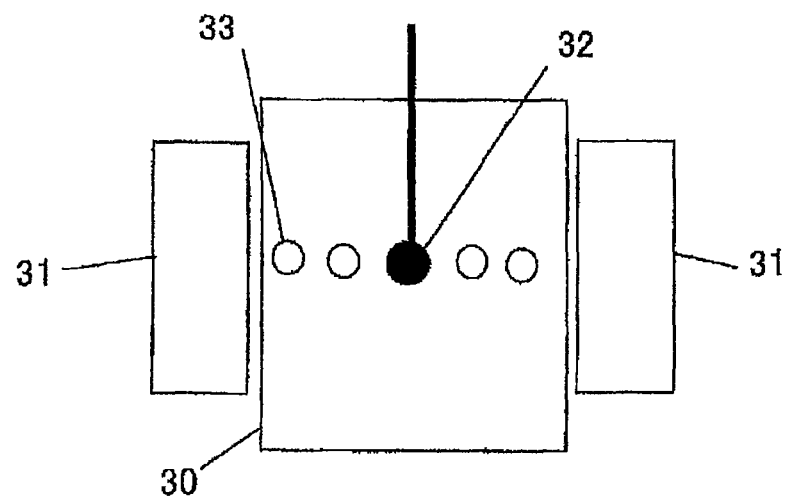
FIG. 9 is a schematic diagram showing an example of a synthetic silica glass molded body to which an inspection lamp is set.

FIG. 9 is a schematic diagram showing an example of the state in which a lamp for inspection is set beside the synthetic silica glass molded body.

FIG. 9 shows the state in which two mercury (Hg) lamps 31 provided with a filter which blocks the visible light are set on the side surfaces of the synthetic silica glass molded body 30 used as a specimen. A fiber probe 32 is disposed on a surface perpendicular to the surface on which a spectrum line of the Hg lamp having a wavelength of 254 nm is irradiated by the mercury (Hg) lamp 31 provided with the filter which blocks the visible light. Such a fiber probe 32 is connected to an unillustrated spectrophotometer. In actually performing an inspection, the measurement is performed in measurement points 33 which are spaced apart form each other at intervals of about 30 mm in the direction parallel to the irradiation direction of the spectrum line while the fiber probe 32 is sequentially moved on the surface perpendicular to the surface on which a spectrum line having a wavelength of 254 nm emitted by the mercury (Hg) lamp 31 provided with the filter which blocks visible light is irradiated.

Figure 10:
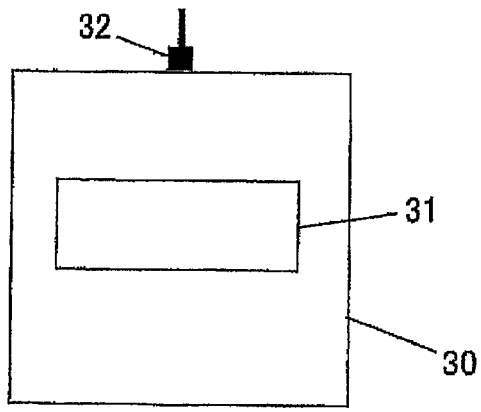
FIG. 10 is a schematic diagram showing the example of the synthetic silica glass molded body to which the inspection lamp is set.

FIG. 10 is a schematic diagram showing the state of the synthetic silica glass molded body 30 shown in FIG. 9 which is viewed from the side on which the mercury (Hg) lamp 31 provided with the filter which blocks the visible light is disposed.

In the present embodiment, setups shown in FIGS. 9 and 10 are made. As the synthetic silica glass molded body 30, a synthetic silica glass molded body having a square surface 200 mm by 200 mm and a thickness of 150 mm is used. Polishing the measurement surface makes it possible to measure fluorescent light intensity and the like with higher sensitivity. Therefore, a surface having a length of 200 mm and a breadth of 150 mm vertical to the square surface is previously polished.

In such a measurement, a spectrum line having a wavelength of 254 nm is irradiated so that the maximum irradiance is about 10 mW/cm² in total using the two mercury (Hg) lamps 31 provided with the filter which blocks the visible light which are set facing to the square surface of the synthetic silica glass molded body 30. Then, fluorescent light spectrum is measured using a fiber type spectrophotometer in a dark room from the direction perpendicular to the irradiation direction of the spectrum line.

In such a measurement, the fluorescent light intensity (spectrum) of a green to a yellow fluorescent light having a center wavelength of 500 nm to 600 nm is measured in each measurement point 33 and recorded, while the fiber probe 32 is linearly shifted at intervals of about 30 mm, as necessary several mm or less, in the direction parallel to the irradiation direction of the spectrum line. At the same time, the intensity of a bright line having a wavelength of 254 nm is measured and recorded.

Then, a ratio (fluorescent light intensity/bright line intensity) of the intensity of a bright line having a wavelength of 254 nm and the intensity of a green to a yellow fluorescent light having a center wavelength of 500 nm to 600 nm which have been obtained by the above measurement is determined. Consequently, a portion which satisfies the condition that the value of the ratio is 0.005 or less is screened out. In such an inspection method, the value is obtained by subtracting a base (dark) from the spectrum within a predetermined wavelength range and by standardizing (so that the bright line intensity is 1) the intensity of the spectrum within the predetermined wavelength range by the bright line intensity of the spectrum having a wavelength of 254 nm which is observed together with the measured fluorescent light. When the value is 0.005 or less, the portion is screened out as an excellent fluorescent light portion. Such an inspection method of the synthetic silica glass molded body makes it possible to conveniently screen out a preferred portion as a material for the production of the synthetic silica glass member used in an exposure apparatus using a light having a short wavelength of 400 nm or less as an exposure light.

A method of inspecting a synthetic silica glass member of the present invention will be described below.

The method of inspecting a synthetic silica glass member, comprises:

a step (a) of irradiating a synthetic silica glass member with $3 \times 10^4$ pulses of a KrF excimer laser light having a wavelength of 248 nm at a repetition frequency of 100 Hz and in an energy density of 100 mJ/(cm²·pulse);

a step (b) of measuring a fluorescent light intensity of yellowish green fluorescent light having a center wavelength of 550 nm emitted by the synthetic silica glass member over the entire surface area of the synthetic silica glass member perpendicular to the irradiation direction of the KrF excimer laser light; and a step (c) of determining whether a condition that a ratio of a minimum value and a maximum value of the fluorescent light intensity of the yellowish green fluorescent light (minimum/maximum) is 0.2 to 1.0 is satisfied or not.

Firstly, the step (a) will be described. The step (a) is the step of irradiating the synthetic silica glass member with $3\times10^4$ pulses of the KrF excimer laser light having a wavelength of 248 nm at a repetition frequency of 100 Hz and in an energy density of 100 mJ/(cm$^2$·pulse).

In the inspection method of the present invention which includes the step (a), the KrF excimer laser having a wavelength of 248 nm is used as the light source. The use of such a KrF excimer laser as the light source allows an ultra minute amount of Cu to be detected with high sensitivity. Therefore it is possible to estimate the distribution of the concentration of Cu which is present in the synthetic silica glass member by means of yellowish green fluorescent light having a center wavelength of 550 nm measured after irradiating KrF excimer laser light. The KrF excimer laser light is preferably irradiated to the synthetic silica glass member in an aluminium-made chamber purged with nitrogen gas the interior In the step (a), $3\times10^4$ pulses of the KrF excimer laser light is irradiated at a repetition frequency of 100 Hz and in an energy density of 100 mJ/(cm$^2$·pulse) on the synthetic silica glass member. The region of the synthetic silica glass member in which Cu has invaded thereby emits yellowish green fluorescent light having a center wavelength of 550 nm. Note that, such a KrF excimer laser is preferably irradiated on the points respectively vertically and horizontally spaced apart from each other at intervals of approximate 30 mm, as necessary several mm or less, corresponding to the following measurement points.

Then, the step (b) will be described. The step (b) is the step of measuring over the entire surface area of the synthetic silica glass member perpendicular to the irradiation direction of the KrF excimer laser light.

In such a step of measuring, the spectrum of yellowish green fluorescent light having a center wavelength of 550 nm is measured using a fluorescence spectrophotometer. Such a measurement is preferably made in each measurement point vertically and horizontally spaced apart from each other at intervals of approximate 30 mm, as necessary several mm or less, over the entire area of the surface on which the KrF excimer laser light is irradiated.

In addition, the step (c) will be described. The step (c) is the step of determining whether a condition that the ratio of the minimum value and the maximum value of the fluorescent light intensity of the yellowish green fluorescent light (minimum/maximum) is 0.2 to 1.0 is satisfied or not.

In the step (c), the ratio of the maximum and minimum values is calculated using the values of the fluorescent light intensity of yellowish green fluorescent light having a center wavelength of 550 nm measured in the above manner. Then, whether the condition that ratio of the minimum and maximum values (minimum/maximum) of the fluorescent light intensity of the yellowish green fluorescent light having a center wavelength of 550 nm is 0.2 to 1.0 is satisfied is judged by using the values obtained by the above calculation.

In the above manner, the KrF excimer laser light is irradiated to measure the distribution of the intensity of fluorescent light having a wavelength of 550 nm. Then, the synthetic silica glass member which satisfies the above condition is screened out, and thereby the synthetic silica glass member which substantially does not cause uneven irradiance of the exposure light transmitted through the synthetic silica glass member can be obtained. That is, such an inspection method makes it possible to screen out a homogeneous synthetic silica glass member which does not cause uneven irradiance.

EXAMPLE

The present invention will more specifically be described below based on Examples and Comparative example. However, the present invention is not limited to the following example.

Example 1

The molding apparatus shown in the above described FIG. 8 was used to mold a synthetic silica glass molded body.

Firstly, a cylindrical synthetic silica glass block 500 mm in diameter and 700 mm in height was immersed in 10%-by-weight aqueous solution of hydrofluoric acid for 24 hours or more, and then sufficiently rinsed with pure water to wash the synthetic silica glass block in advance.

High purity carbon powders in which a content of Cu is 40 wt.ppb and a content of Al is 100 wt.ppb were placed in a furnace for pretreatment, and then pre-heated at conditions of 3 Pa and 1800° C. for 3 hours. In addition, a mold was placed in the furnace for pretreatment, and then pre-heated at conditions of 3 Pa and 1800° C. for 3 hours. Then, the pre-heated high purity carbon powders were applied on the inner surface of the pre-heated mold so that the applied amount was 10 mg/cm$^2$.

Next, the washed cylindrical synthetic silica glass block was left at rest in the mold on which the pre-heated high purity carbon powders were applied. The content of Cu in the mold used here was 140 wt.ppb. Then, the pressure in the furnace was reduced to 10 Pa using a vacuum pump. Thereafter, the furnace was filled with a pure nitrogen gas at a pressure of $1\times10^4$ Pa, heated at a temperature increasing rate of 400° C./hour over a period of 3 hours, and maintained at a temperature condition of 1600° C. for 30 minutes. Subsequently, a synthetic silica glass molded body was molded by applying the maximum pressing force of 0.4 kg/cm$^2$ by means of a cylinder rod from vertically above of the mold. Note that, the time period necessary for such molding was 1 hour. The heat generation by a heater was stopped after molding. The mold was left standing for 20 hours to cool naturally. Thus, a plate-like synthetic silica glass molded body having a square surface 1000 mm on a side and 137 mm in thickness was obtained.

By cutting the synthetic silica glass molded body having a square surface 1000 mm on a side and 137 mm in thickness which was produced by such a producing method of the synthetic silica glass molded body of the present invention, 25 samples each with a rectangular form having a square surface 200 mm on a side and 137 mm in thickness was obtained. The square surface 200 mm on a side of such a sample is perpendicular to the direction in which the pressing force was applied at the time of molding. A spectrum line of two mercury (Hg) lamps having a wavelength of 254 nm transmitted through a visible light-blocking filter was irradiated at an irradiance of 10 mW/cm$^2$ in total to the sample from the direction perpendicular to the square surface 200 mm on a side. Then, the bright line intensity of a spectrum line having a wavelength of 254 nm and the fluorescent light intensity of fluorescent light having a center wavelength of 500 nm to 600 nm were measured from the direction perpendicular to the irradiation direction of the spectrum line in a dark room.

Figure 11:
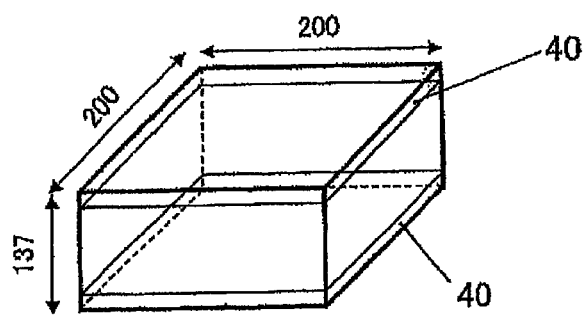
FIG. 11 is a schematic diagram showing the state of a portion in which a fluorescent light is observed, and the state of a portion in which a fluorescent light is not observed.

As a result of the measurement, a green fluorescent light was observed to a depth of 3 mm from the square surface 200 mm on a side. The ratio of the bright line intensity and the fluorescent light intensity was 0.005 or more. In all the samples, the depth from the top and bottom square surfaces in which the above described fluorescent light was observed was the same. FIG. 11 is a schematic diagram showing the states of the portion in which the fluorescent light is observed, and of the portion in which the fluorescent light is not observed.

Then, the region in which the fluorescent light was observed, i.e. the top and bottom square surface portions having a thickness of 3 mm was removed from such a sample by grinding to produce a synthetic silica glass member.

Figure 12:
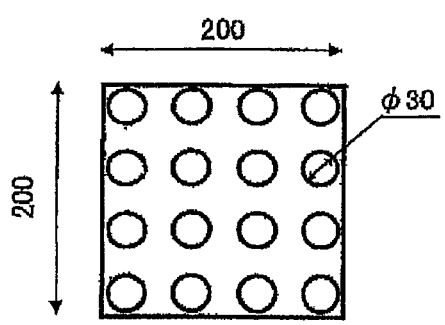
FIG. 12 is a schematic diagram showing positions where cylindrical blocks are cut out when the blocks are cut out of a synthetic silica glass member.

16 (crosswise 4×lengthwise 4) cylindrical blocks 30 mm in diameter and 131 mm in thickness were cut out at equal intervals in the direction perpendicular to the square surface 200 mm on a side of such a synthetic silica glass member. FIG. 12 is a schematic diagram showing the positions where the cylindrical blocks are cut out when the blocks are cut out from the synthetic silica glass member.

Each cylindrical block cut out in the above manner was further sliced at intervals of a thickness of 13.1 mm into ten equal pieces, and thereby producing cylindrical sample pieces 30 mm in diameter and 13.1 mm in thickness. The both surfaces of the sample piece obtained in the above manner were equally grinded and polished, and thereby producing an evaluation sample 30 mm in diameter and 10 mm in thickness.

Firstly, the transmittance of the evaluation sample was measured. Optical transmittance measurement in near infrared-ultraviolet area was made using a commercially available double-beam type spectrophotometer to determine a transmittance. In such a measurement, using a halogen lamp and a deuterium lamp as a light source in near-infrared area and in ultraviolet area, respectively, the light dispersed by a diffraction grating was separated into two rays comprising a reference ray and a measurement ray. Both of the separated rays were introduced into a sample room purged with a nitrogen gas. At this time, nothing was placed on a sample stage on the reference ray side. Meanwhile, the evaluation sample was left at rest on a sample stage on the measurement ray side. Then, the reference ray and measurement ray transmitted through the sample room were collected by means of an integrating sphere, and reference ray intensity A and measurement ray intensity A were detected using a photomultiplier. Moreover, reference ray intensity B and measurement ray intensity B were detected in the same manner as described above except that the evaluation sample was not placed on the sample stages on both the reference ray side and the measurement ray side. Then, the values of the reference ray intensity A and B and the measurement ray intensity A and B which were measured in the above manner were introduced into the following equation to calculate their transmittance.

(Transmittance)=(measurement ray intensity $A$/reference ray intensity $A$)÷(measurement ray intensity $B$/reference ray intensity $B$)

The transmittances of the evaluation samples obtained in the above manner were 90.6% (deviation of ±0.1% between samples) in a case of a wavelength of 193 nm, and 92.1% (deviation of ±0.05 between samples) in a case of a wavelength of 248 nm. This shows that absolute values were high, that the distribution thereof was small, and thereby that the obtained synthetic silica glass has a high quality.

Then, the laser resistance of the evaluation sample was evaluated. In such a laser resistance test, a KrF excimer laser having a wavelength of 248 nm was used as laser. The irradiation of the KrF excimer laser light to the evaluation sample was performed in an aluminium-made chamber purged with a nitrogen gas. At this time, a circular surface 30 mm in diameter was stood upright. Then, the KrF excimer laser was irradiated from the direction perpendicular to the circular surface 30 mm in diameter at an energy density of 50 mJ/(cm$^2$·pulse) and in the pulse number of $3\times10^4$. Thereafter, the fluorescent light during the irradiation of the KrF excimer laser was visually observed in the dark room. As a result of the observation, among the samples, low intensity yellow fluorescent light was observed in the uppermost and lowermost stages of the cylindrical block from which the evaluation samples were not cut out. Thereafter, the irradiation was continued to the pulses of $1\times10^6$. Then, the sample was taken out of the chamber, and the transmittance of a wavelength of 248 nm was measured in the above method. As a result of the measurement, the substantial reduction in the transmittance was not found both in the evaluation sample in which yellow fluorescent light was not observed, and also even in the evaluation sample in which yellow fluorescent light was observed.

Subsequently, the impurity concentration in the evaluation samples was measured. The impurity concentration in the evaluation samples was measured by analysis by ICP-MS. As a result of the measurement, in all the samples, the concentration of Cu was less than 0.1 wt.ppb, which is the lower detection limit. In addition, the concentration of Al was less than 6 ppb. Therefore, all the evaluation samples satisfied the condition indicated by the following equation (1):

$$[Cu]+0.03\times[Al]<0.4 \text{ wt.ppb} \tag{1}$$

Comparative Example 1

A synthetic silica glass molded body was molded in the same manner as that of Example 1 except that a synthetic silica glass block was not previously washed in molding the synthetic silica glass molded body for the purpose of comparison. 25 samples each with a rectangular form having a square surface 200 mm on a side and 137 mm in thickness were obtained in the same manner as that of Example 1.

With respect to such samples, the bright line intensity of the spectrum line having a wavelength of 254 nm, and the fluorescent light intensity of fluorescent light having a center wavelength of 500 nm to 600 nm were measured in the same manner as that of Example 1. As a result of the measurement, a green fluorescent light was observed to a depth of 35 mm (70 mm in total on the top and bottom portions) from the square surface 200 mm on a side. The ratio of the bright line intensity and the fluorescent light intensity was 0.005 or more.

Here, the physical properties of the portion (near the 200 mm×200 mm surface) in which the ratio of the bright line intensity and the fluorescent light intensity was 0.005 or more was daringly measured.

For such measurement, evaluation samples 30 mm in diameter and 10 mm in thickness were produced in the same manner as that of Example 1. Then, the transmittance, laser resistance and impurities of the evaluation samples were measured in the same manner as that of Example 1.

As a result of the measurement, the transmittance was as low as 91.0% in a case of a wavelength of 248 nm, and very intense yellow fluorescent light was observed during the irradiation of laser. The transmittance of the evaluation sample was 88.9% after the KrF excimer laser was irradiated under the same conditions as those of Example 1. This was 1% of reduction in the transmittance from the initial transmittance. In addition, the concentrations of impurities of Cu and Al were 1 wt.ppb and 15 wt.ppb, respectively. Furthermore, the value of the equation (1), i.e. the value obtained by calculation using the equation of [Cu]+0.03×[Al] was 3.3. This was much more than 0.4.

As apparent from these results, it was confirmed that the synthetic silica glass molded body obtained by the method of molding a synthetic silica glass molded body of the present invention in the same manner as that of Example 1 did not emit an intense yellow fluorescent light which has an influence on an exposure performance during the irradiation of laser in a very wide region of 95.6% by volume thereof, and had a very excellent quality including the transmittance and laser resistance which have influence directly on the exposure performance.

In contrast, a portion of the synthetic silica glass molded body in which the ratio of the bright line intensity and the fluorescent light intensity was 0.005 or more (hereinafter referred to as defective portion) accounted for 50% or more in the synthetic silica glass molded body obtained by the conventional method of molding a synthetic silica glass molded body as described in Comparative example 1. In addition, the defective portion had a low transmittance and low laser resistance. As a result, it was realized that it was substantially difficult to cost-effectively produce a synthetic silica glass member used in an exposure apparatus using a light having a short wavelength of 400 nm or less as an exposure light by the conventional method of molding a synthetic silica glass molded body.

Example 2

A synthetic silica glass molded body was molded in the same manner as that of Example 1 except that a synthetic silica glass block was not previously washed in molding the synthetic silica glass molded body. Then, 25 samples each with a rectangular form having a square surface 200 mm on a side and 137 mm in thickness were obtained in the same manner as that of Example 1.

With respect to such samples, the bright line intensity of the spectrum line having a wave length of 254 nm, and the fluorescent light intensity of fluorescent light having a center wavelength of 500 nm to 600 nm were measured in the same manner as that of Example 1. Then, a portion (hereinafter, passing portion) which satisfied the condition that the ratio of the bright line intensity and the fluorescent light intensity which were obtained in the above measurement was 0.005 or less, and a portion (hereinafter, defective portion) which did not satisfy the same condition were inspected. As a result of the inspection, the defective portions were present on the top and at the bottom in the sample to each depth of 30 mm from the square surface 200 mm on a side.

An evaluation sample 30 mm in diameter and 10 mm in thickness was produced from the above sample in the same manner as that of Example 1. With respect to the downwardly and upwardly third evaluation samples from the surfaces corresponding to the square surfaces 200 mm on a side in the samples produced from the defective portion, and with respect to the fourth evaluation samples from the surfaces corresponding to the square surfaces 200 mm on a side in the samples produced from the passing portion, the transmittance and the impurity concentration were measured in the same manner as that of Example 1.

The transmittance of the evaluation sample produced from the passing portion was 90.6% in the case of a light having a wavelength of 193 nm, and 92.1% in the case of a light having a wavelength of 248 nm. With respect to the transmittance of the evaluation sample produced from the defective portion, the transmittance of the light having a wavelength of 193 nm was lower by 0.3% than the evaluation sample produced from the passing portion. The transmittance of the light having a wavelength of 248 nm was 92.1%.

The impurity concentration in the evaluation sample produced from the passing portion was 0.1 wt.ppb for copper and 6 wt.ppb for aluminium. Furthermore, the value of the equation (1) was 0.3. In contrast, the impurity concentration in the evaluation sample produced from the defective portion was 0.2 wt.ppb for copper and 7 wt.ppb for aluminium. Furthermore, the value of the equation (1) was 0.4.

It was realized that the passing portion screened out by measuring the fluorescent light when a spectrum line having a wavelength of 254 nm was irradiated at an irradiance condition of 10 mW/cm$^2$ or more was passing with respect to the transmittance. It was realized from such results that the portion screened out by the above fluorescent light inspection satisfied the conditions that the concentrations of copper and aluminium were 0.2 wt.ppb or less and 10 wt.ppb or less, respectively, and that the concentrations of copper and aluminium were represented by the following equation (1):

$$[Cu]+0.03\times[Al]<0.4 \text{ wt.ppb} \qquad (1)$$

where [Cu] shows the concentration of copper and [Al] shows the concentration of aluminium.

Meanwhile, the defective portion screened out in the same manner had a significantly-reduced transmittance in a deep ultraviolet area as compared to that of the passing portion. This is because the invasion length of Cu and the invasion length of Na are approximately the same. The following effect was found from the results. Specifically, by measuring fluorescent light when a spectrum line having a wavelength of 254 nm is irradiated at an irradiance condition of 10 mW/cm$^2$ to screen out the passing portion and the defective portion, Cu can be detected with very high sensitivity. Then, the use of Cu as a probe had an influence on the transmittance, but allows to exclude the contamination region due to Na which is difficult to detect. In other words, it can be said that the fluorescent light intensity measured in the method of inspecting a synthetic silica glass molded body of the present invention not only indicates the fluorescent light intensity due to Cu contamination, but also reflects the qualities including the transmittance, laser resistance, and the like which have an influence directly on the exposure performance. Therefore, the synthetic silica glass member produced using the passing portion screened out by using the method of inspecting a synthetic silica glass molded body of the present invention does not emit intense yellow fluorescent light which has an influence on the exposure performance during the irradiation of laser, but also has very excellent transmittance which has an influence directly on the exposure performance. In contrast, the synthetic silica glass member produced using the defective portion screened out by the inspection method according to the present invention emits intense fluorescent light which has an influence on the exposure performance during the irradiation of laser, as well as experiences a significant reduction in the transmittance which has an influence directly on the exposure performance.

Example 3

A synthetic silica glass molded body was molded in the same manner as that of Example 1 except that a synthetic silica glass block was not previously washed in molding the synthetic silica glass molded body. Then, 25 samples each with a rectangular form having a square surface 200 mm on a side and 137 mm in thickness were obtained in the same manner as that of Example 1.

Figure 13:
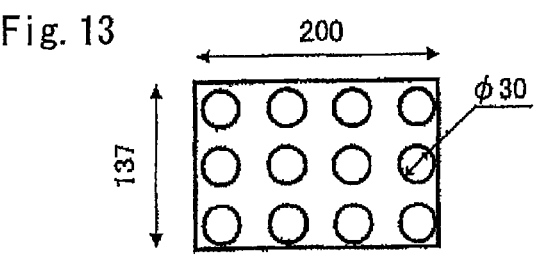
FIG. 13 is a schematic diagram showing positions where cylindrical blocks are cut out, when the blocks are cut out of a sample.

Then, cylindrical blocks (4 (in a direction of 200 mm side)×3 (in a direction of 137 mm side)=12 pieces) 30 mm in diameter and 200 mm in thickness were cut out from the above sample in the direction perpendicular to a surface having the side 200 mm long and the side 137 mm long. FIG. 13 is a schematic diagram showing the cut-out positions when the cylindrical blocks are cut out from the sample.

The cylindrical block cut out in the above manner was further sliced at intervals of a thickness of 13.3 mm into fifteen equal pieces. The both surfaces of the obtained slice were equally grinded and polished, and thereby obtaining a cylindrical evaluation sample 30 mm in diameter and 10 mm in thickness. Every 12 pieces of the evaluation samples, obtained in the above manner, from each edge of the cylindrical blocks were dealt with as a set. Then, the physical properties of each set were compared. When the synthetic silica glass member including a surface having a side 200 mm long and a side 137 mm long was obtained by slicing the sample in parallel to a surface having a side 200 mm long and a side 137 mm long, the above comparison of the physical properties of the evaluation sample is equivalent to the measurement of the in-plane distribution of the qualities of the member.

Firstly, the transmittance of the evaluation sample of above each set was measured in the same manner as that of Example 1. As a result of the measurement, it was found that there was the distribution of transmittances in which the transmittance was reduced in upward and downward direction (toward the side 200 mm long) from the center of the surface having the side 200 mm long and the side 137 mm long when a synthetic silica glass member including the surface having the side 200 mm long and the side 137 mm long. The reduction amount of the transmittance in the portion (evaluation samples contacting the side 200 mm long (4 pieces+4 pieces) in which the transmittance was significantly reduced was about 1.0% lower in the case of a wavelength of 193 nm than four pieces of the samples located in the center, and about 1.0% further lower in the case of a wavelength of 248 nm. On the other hand, the distribution of the transmittance was not found in the direction perpendicular to the side 137 mm long. This pattern was found in the group of the evaluation samples of any set.

Then, the KrF excimer laser light was irradiated to the evaluation sample to observe fluorescent light. That is, the irradiation of the KrF excimer laser light to the evaluation sample was performed in the aluminium-made chamber purged with a nitrogen gas. The circular surface 30 mm in diameter of the sample was stood upright. Then, the KrF excimer laser was irradiated from the direction perpendicular to the circular surface 30 mm in diameter at a repetition frequency of 100 Hz and in an energy density of 100 mJ/(cm$^2$·pulse). Then, the KrF excimer laser light was irradiated in a pulse number of $3 \times 10^4$. Thereafter, the spectrum of yellowish green fluorescent light having a center wavelength of 550 nm emitted by the evaluation sample was measured using a fluorescence spectrophotometer. Comparison between sets of samples was made with respect to the height of the peak of the spectrum of yellowish green fluorescent light having a center wavelength of 550 nm measured in the above manner. The measured intensity of yellow fluorescent light was very intense in the evaluation samples (4 pieces+4 pieces) contacting the side 200 mm long. Meanwhile, the intensity of yellow fluorescent light was very low in the evaluation samples (4 pieces) which were located in the center and not contacted the side 200 mm long. The ratio of the fluorescent light intensity relative to the edge portion (fluorescent light intensity of the center portion (minimum value))/(fluorescent light intensity of the edge portion (maximum value)) was about 0.1. This pattern was found in the group of the samples of any set. On the other hand, the intensity of yellow fluorescent light observed in the evaluation sample which is located in the center and not contacted the side 200 mm long was compared using the evaluation sample located in the direction in which the cylindrical block was cut out. In this case, the difference in fluorescent light intensity was small. The ratio of fluorescent light intensity (minimum fluorescent light intensity/maximum fluorescent light intensity) was 0.8. It was found from this result that the sample which was located in the center and was not contacted the side 200 mm long was a fluorescent light passing portion, and provided a small fluctuation of fluorescent light intensity.

It was found from this result that it is possible to obtain a synthetic silica glass member which has a small distribution of the transmittance, i.e. substantially does not causes irradiance fluctuation of the exposure light transmitted through the synthetic silica glass member when the distribution of fluorescent light intensity of a wavelength of 550 nm is measured to screen out a passing portion by irradiating the KrF excimer laser light in the above manner. On the other hand, it was also found that the synthetic silica glass member which is judged to be a defective portion by measuring the distribution of the fluorescent light intensity in the above manner causes irradiance fluctuation of the exposure light transmitted through the member, and thereby the exposure performance is notably reduced.

As described above, according to the present invention, it becomes possible to provide: a method of molding a synthetic silica glass molded body which makes it possible to obtain, surely and with high efficiency, a synthetic silica glass molded body in which a defective portion due to impurity contamination is fully prevented from occurring irrespective of the fact that the method is a method of molding a synthetic silica glass molded body by heating and pressing molding method; a synthetic silica glass molded body which makes it possible to improve a yield of a high quality synthetic silica glass member used in an exposure apparatus in which the light having a short wavelength of 400 nm or less is used as an exposure light; and a method of inspecting a synthetic silica glass member which makes it possible to screen a defective portion due to impurity contamination which is present in the synthetic silica glass molded body.

Accordingly, the method of molding a synthetic silica glass molded body of the present invention is excellent in preventing defective portions due to impurity contamination from occurring, and therefore particularly useful as an industrial manufacturing method of a synthetic silica glass molded body used as a material for producing a high quality synthetic silica glass member used in an exposure apparatus using the light having a short wavelength of 400 nm or less as an exposure light.

What is claimed is:

1. A method of inspecting a synthetic silica glass molded body, comprising:
   irradiating the synthetic silica glass molded body with a spectrum line of an Hg lamp having a wavelength of 254 nm, at an irradiance condition of 10 mW/cm$^2$ or more, which has been transmitted through a filter for any one of blocking a visible light and reducing an intensity thereof;
   measuring, in a direction perpendicular to the irradiation direction of the spectrum line, an intensity of a bright line having a wavelength of 254 nm emitted by the synthetic silica glass molded body, and a fluorescent light intensity from a green to a yellow fluorescent light having a center wavelength of 500 nm to 600 nm emitted by the synthetic silica glass molded body; and screening a portion which satisfies a condition that a ratio of the bright line intensity and the fluorescent light intensity (fluorescent light intensity/bright line intensity) is 0.005 or less.

2. The method of inspecting a synthetic silica glass molded body according to claim 1, wherein a measurement surface of the synthetic silica glass molded body is previously polished.

3. A method of inspecting a synthetic silica glass member, comprising:

irradiating the synthetic silica glass member with $3\times10^4$ pulses of a KrF excimer laser light having a wavelength of 248 nm at a repetition frequency of 100 Hz and in an energy density of 100 mJ/(cm$^2$·pulse);

measuring a fluorescent light intensity of yellowish green fluorescent light having a center wavelength of 550 nm emitted by the synthetic silica glass member over the entire surface area of the synthetic silica glass member perpendicular to the irradiation direction of the KrF excimer laser light; and determining whether a condition that a ratio of a minimum value and a maximum value of the fluorescent light intensity of the yellowish green fluorescent light (minimum/maximum) is 0.2 to 1.0 is satisfied or not.

4. The method of inspecting a synthetic silica glass member according to claim 3, wherein the irradiating the KrF excimer laser light is performed in an aluminum-made chamber purged with a nitrogen gas.

\* \* \* \* \*

UNITED STATES PATENT AND TRADEMARK OFFICE
CERTIFICATE OF CORRECTION

PATENT NO. : 8,679,994 B2
APPLICATION NO. : 13/961499
DATED : March 25, 2014
INVENTOR(S) : Mizuguchi It is certified that error appears in the above-identified patent and that said Letters Patent is hereby corrected as shown below:

On the Title Page Item [54] and in the Specification, Column 1, Line 2 (Title), delete "SILICIA" and insert -- SILICA --, therefor.

Signed and Sealed this
First Day of July, 2014

Michelle K. Lee
*Deputy Director of the United States Patent and Trademark Office*